(12) United States Patent
Novak et al.

(10) Patent No.: US 6,268,384 B1
(45) Date of Patent: Jul. 31, 2001

(54) COMPOUNDS POSSESSING NEURONAL ACTIVITY

(75) Inventors: Perry M. Novak, Milford; Michael Mullican, Needham, both of MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/085,441

(22) Filed: May 27, 1998

Related U.S. Application Data

(63) Continuation-in-part of application No. 08/920,838, filed on Aug. 29, 1997, now abandoned.

(51) Int. Cl.$^7$ .......................... A61K 31/44; C07D 213/81
(52) U.S. Cl. .......................... 514/332; 514/357; 514/318; 546/265; 546/337; 546/193; 546/194
(58) Field of Search .................. 546/265, 337, 546/193, 194; 514/332, 357, 318

(56) References Cited

U.S. PATENT DOCUMENTS

| 5,543,423 | 8/1996 | Zelle et al. ............................. 514/332 |
| 5,614,547 | 3/1997 | Hamilton et al. ...................... 514/423 |
| 5,696,135 | 12/1997 | Steiner et al. ......................... 514/317 |
| 5,721,256 | * 2/1998 | Hamilton et al. ...................... 514/330 |
| 5,744,485 | * 4/1998 | Zelle et al. ............................. 514/318 |

FOREIGN PATENT DOCUMENTS

| WO 92/21313 | 12/1992 | (WO) . |
| WO 94/07858 | 4/1994 | (WO) . |
| WO 95/26337 | 10/1995 | (WO) . |
| WO 96/15101 | 5/1996 | (WO) . |
| WO 96/40140 | 12/1996 | (WO) . |
| WO 96/40633 | 12/1996 | (WO) . |
| WO 97/16190 | 5/1997 | (WO) . |

OTHER PUBLICATIONS

CA 126:74600, Dyke et al., 1997.*
CA 126:30933, Defauw et al., 1996.*
CA 127:262477, Fukuyama et al., 1997.*
CA 99:195371, Ikota et al., 1983.*
J.P. Steiner et al., "High brain densities of the immunophilin FKBP colocalized with calcineurin," *Nature*, 358, pp. 584–587 (1992).
J.R. Hauske et al., "Design and synthesis of novel FKBP inhibitors," *J. Med. Chem.*, 35, pp. 4284–4296 (1992).
B.G. Gold et al., "FK506, an immunosuppressant, increases functional recovery of axonal regeneration in the rat following axotomy of the sciatic nerve," *Soc. Neurosci. Abs.*, 19, p. 1316 (1993).
B.G. Gold et al., "The immunosuppressant FK506 increases the rate of axonal regeneration in rat sciatic nerve," *J. Neuroscience.*, 15(11), pp. 7509–7516 (Nov., 1995).
W.E. Lyons et al., "Immunosuppressant FK506 promotes neurite outgrowth in cultures of PC12 cells and sensory ganglia," *Proc. Natl. Acad. Sci. USA*, 91, pp. 3191–3195 (Apr., 1994).
J. Sharkey et al., "Immunophilins mediate the neuroprotective effects of FK506 in focal cerebral ischaemia," *Nature*, 371 pp. 336–339 (Sep. 22, 1994).
W.E. Lyons et al., "Neuronal regeneration enhances the expression of the immunophilin FKBP-12," *J. Neuroscience.*, 15, pp. 2985–2994 (Apr., 1995).
B. R. Baker and Jeffrey A. Hurlbut, "Irreversible Enzyme Inhibitors. CLVI. Proteolytic Enzymes. XII. Inhibitors of Guinea Pig Complement Derived by Quaternization of 3–Acylamidopyridines with α–Bromomethylbenzenesulfonyl Fluorides," *J. Med. Chem.*, 12, pp. 677–680 (Jul. 1969).
Cynthia Deyrup and Ben M. Dunn, "A New Substrate for Porcine Pepsin Possessing Cryptic Fluorescence Properties," *Anal. Biochem.*, 129, pp. 502–512, (1983).

* cited by examiner

*Primary Examiner*—Jane Fan
(74) *Attorney, Agent, or Firm*—Fish & Neave; James F. Haley, Jr.; Nina R. Horan

(57) ABSTRACT

The present invention relates to compounds, methods and pharmaceutical compositions for stimulating the growth of neurites in nerve cells. The compounds and the compositions and methods that utilize them can be used, either alone or in conjunction with a neurotrophic factor, such as nerve growth factor, to promote repair of neuronal damage caused by disease or physical trauma.

10 Claims, No Drawings

COMPOUNDS POSSESSING NEURONAL ACTIVITY

CROSS-REFERENCE TO RELATED APPLICATION

This application is a continuation-in-part of U.S. patent application Ser. No. 08/920,838, filed Aug. 29, 1997 now abandoned.

TECHNICAL FIELD OF THE INVENTION

The present invention relates to compounds, methods and pharmaceutical compositions which possess neuronal activity. The compounds and compositions that can be used either alone or in conjunction with a neurotrophic factor, such as nerve growth factor, in methods for treating or preventing neuronal damage caused by disease or physical trauma.

BACKGROUND OF THE INVENTION

Neurological diseases are associated with the death of or injury to neuronal cells. For example, the loss of dopaminergic neurons in the substantia nigra is the basis for Parkinson's disease. Although the molecular mechanism of neurodegeneration in Alzheimer's disease is yet to be established, inflammation and deposition of beta-amyloid protein and other such agents may compromise neuronal function or survival. In patients suffering from brain ischemia or spinal cord injuries, extensive neuronal cell death is observed. Currently, there are no satisfactory treatments for these diseases.

One approach to treating neurological diseases involves the use of drugs capable of inhibiting neuronal cell death. A more recent approach involves the promotion of nerve regeneration by drugs which stimulate neurite outgrowth.

Neurite outgrowth may be stimulated in vitro by nerve growth factors, such as NGF. For example, Glial Cell Line-Derived Neurotrophic Factor (GDNF) demonstrates neurotrophic activity both, in vivo and in vitro, and is currently being investigated for the treatment of Parkinson's disease. Insulin and Insulin-like growth factors have been shown to stimulate growth of neurites in rat pheochromocytoma PC12 cells and in cultured sympathetic and sensory neurons [Recio-Pinto et al., *J. Neurosci.,* 6, pp. 1211–1219 (1986)]. Insulin and Insulin-like growth factors also stimulate the regeneration of injured motor nerves in vivo and in vitro [Near et al., *PNAS,* pp. 89, 11716–11720 (1992); and Edbladh et al., *Brain Res.,* 641, pp. 76–82 (1994)]. Similarly, fibroblast growth factor (FGF) stimulates neural proliferation [D. Gospodarowicz et al., *Cell Differ.,* 19, p. 1 (1986)] and growth [M. A. Walter et al., *Lymphokine Cytokine Res.,* 12, p. 135 (1993)].

There are, however, several disadvantages associated with the use of nerve growth factors for treating neurological diseases. They do not readily cross the blood-brain barrier. They are unstable in plasma. And they have poor drug delivery properties.

Recently, small molecules have been shown to stimulate axonal outgrowth in vivo. In individuals suffering from a neurological disease, this stimulation of neurite outgrowth may protect neurons from further degeneration, and accelerate the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.,* 56, pp. 169–78 (1996); and B. S. McEwen et al., *Brain Res. Dev. Brain. Res.,* 87, pp. 91–95 (1995)]. The progress of Alzheimer's disease may be slowed in women who take estrogen. Estrogen is hypothesized to complement NGF and other neurotrophins and thereby help neurons differentiate and survive.

It has been reported that compounds with an affinity for the FK506 binding protein (FKBP) that inhibit that protein's rotamase activity also possess nerve growth stimulatory activity. [Lyons et al., *PNAS,* 91, pp. 3191–3195 (1994)]. Many of these such compounds also have immunosuppressive activity.

FK506 (Tacrolimus), an immunosuppressive drug, has been demonstrated to act synergistically with NGF in stimulating neurite outgrowth in PC12 cells as well as sensory ganglia [Lyons et al. (1994)]. This compound has also been shown to be neuroprotective in focal cerebral ischemia [J. Sharkey and S. P. Butcher, *Nature,* 371, pp. 336–339 (1994)] and to increase the rate of axonal regeneration in injured sciatic nerve [B. Gold et al., *J. Neurosci.,* 15, pp. 7509–16 (1995)].

The use of immunosuppressive compounds, however, has obvious drawbacks. In addition to compromising immune function, prolonged treatment with these compounds can cause nephrotoxicity [Kopp et al., *J. Am. Soc. Nephrol.,* 1, p. 162 (1991)], neurological deficits [P.C. DeGroen et al., *N. Eng. J. Med.,* 317, p. 861 (1987)] and vascular hypertension [Kahan et al., *N. Eng. J. Med.,* 321, p. 1725 (1989)].

More recently, sub-classes of FKBP binding compounds which inhibit rotamase activity, but which purportedly lack immunosuppressive activity have been disclosed for use in stimulating nerve growth [see U.S. Pat. Nos. 5,614,547; 5,696,135; WO 96/40633; WO 96/40140; WO 97/16190; J. P. Steiner et al., *Proc. Natl. Acad. Sci. USA,* 94, pp. 2019–23 (1997); and G. S. Hamilton et al., *Bioorg. Med. Chem. Lett.,* 7, pp. 1785–90 (1997)]. While these compounds supposedly avoid certain unwanted side effects of immunosuppressive FKBP binding compounds, they still bind to FKBP and inhibit its rotamase activity. This latter property may still lead to undesirable side effects due to other roles FKBP may play in mammals.

Surprisingly, it is now known that binding to FKBP is not necessary for neuronal activity. Co-pending U.S. patent application Ser. Nos. 08/748,447, 08/748,448 and 08/749, 114 each describe the use of non-FKBP binding, non-immunosuppressive compounds for stimulating nerve growth and preventing neurodegeneration. Due to their lack of affinity for FKBP, these compounds advantageously avoid any potential interference with FKBP-associated biochemical pathways. These compounds do, however, inhibit multi-drug resistance ("MDR") through inhibition of the p-glycoprotein and MRP. While it appears that the dosages of those compounds necessary to stimulate nerve growth and prevent neurodegeneration are lower than those that effect MDR, it would still be desirable to obtain compounds which are specific for neuronal activity, without other significant mechanisms of action.

Though a wide variety of neurological degenerative disorders may be treated by stimulating neurite outgrowth, there are relatively few agents known to possess these properties. Moreover, the newer non-immunosuppressive compounds have only recently begun being tested in living organisms. Thus, there remains a need for new pharmaceutically acceptable compounds and compositions that have the ability to stimulate neurite outgrowth and prevent neurodegeneration in patients without causing immunosuppression, without interfering with FKBP and without affecting cellular pumps, such as p-glycoprotein or MRP.

SUMMARY OF THE INVENTION

Applicants have identified several subclasses of compounds that do not bind FKBP, do not inhibit MDR, but have potent neuronal activity.

The term "neuronal activity", as used herein, includes stimulation of damaged neurons, promotion of neuronal regeneration, prevention of neurodegeneration and treatment of a neurological disorder. The compounds of this invention have activity in both peripheral nerves and the central nervous system.

Two of these subgenera fall within the genus of compounds described in WO 92/21313. These compounds are characterized by the formulae:

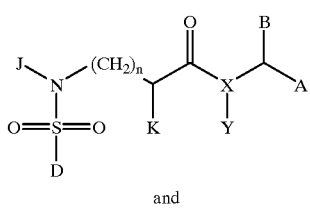

(I)

and

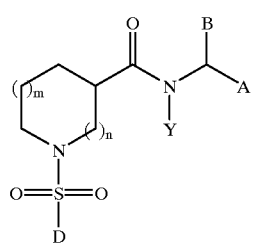

(II)

Two other subgenera of compounds of this invention have the formulae:

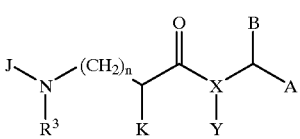

(III)

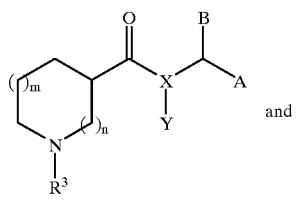

(IV)

and

The invention also includes pharmaceutically acceptable derivatives of any of compounds (I) through (IV).

In each of these compounds, A and B are independently selected from hydrogen, Ar, ($C_1$–$C_6$)-straight or branched alkyl, ($C_2$–$C_6$)-straight or branched alkenyl or alkynyl, ($C_5$–$C_7$)-cycloalkyl substituted-($C_1$–$C_6$)-straight or branched alkyl, ($C_5$–$C_7$)-cycloalkyl substituted-($C_2$–$C_6$)-straight or branched alkenyl or alkynyl, ($C_5$–$C_7$) cycloalkenyl substituted-($C_1$–$C_6$)-straight or branched alkyl, ($C_5$–$C_7$)-cycloalkenyl substituted- ($C_2$–$C_6$)-straight or branched alkenyl or alkynyl, Ar-substituted-($C_1$–$C_6$)-straight or branched alkyl, or Ar-substituted-($C_2$–$C_6$)-straight or branched alkenyl or alkynyl; wherein any one of the $CH_2$ groups of said alkynyl, alkenyl or alkyl chains in A or B is optionally replaced by O, S, S(O), S(O)$_2$ or N(R); wherein R is selected from hydrogen, ($C_1$–$C_6$)-straight or branched alkyl, or ($C_2$–$C_6$)-straight or branched alkenyl or alkynyl;

Ar is selected from phenyl, 1-naphthyl, 2-naphthyl, indenyl, azulenyl, fluorenyl, anthracenyl, 2-furyl, 3-furyl, 2-thienyl, 3-thienyl,2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isothiazolyl, 1,2,3-oxadiazolyl, 1,2,3-triazolyl, 1,2,3-thiadiazolyl, 1,3,4-thiadiazolyl, 1,2,4-triazolyl, 1,2,4-oxadiazolyl, 1,2,4-thiadiazolyl, benzoxazolyl, pyridazinyl, pyrimidinyl, pyrazinyl, 1,3,5-triazinyl, 1,3,5-trithianyl, indolizinyl, indolyl, isoindolyl, 3Hindolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-isoquinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl or other chemically feasible monocyclic, bicyclic or tricyclic ring systems, wherein each ring consists of 5 to 7 ring atoms and wherein each ring comprises 0 to 3 heteroatoms independently selected from N, N(R), O, S, S(O), or S(O)$_2$ and wherein each Ar is optionally substituted with one to three substituents independently selected from halogen, hydroxyl, nitro, —SO$_3$H, trifluoromethyl, trifluoromethoxy, ($C_1$–$C_6$)-straight or branched alkyl, ($C_2$–$C_6$)-straight or branched alkenyl, O-[($C_1$–$C_6$)-straight or branched alkyl], O-[($C_2$–$C_6$)-straight or branched alkenyl], O-benzyl, O-phenyl, 1,2-methylenedioxy, —N(R$^1$) (R$^2$), carboxyl, N-($C_1$–$C_5$-straight or branched alkyl or $C_2$–$C_5$-straight or branched alkenyl) carboxamides, N,N-di-($C_1$–$C_5$-straight or branched alkyl or $C_2$–$C_5$-straight or branched alkenyl) carboxamides, N-($C_1$–$C_5$-straight or branched alkyl or $C_2$–$C_5$-straight or branched alkenyl) sulfonamides, N,N-di-($C_1$–$C_5$-straight or branched alkyl or $C_2$–$C_5$-straight or branched alkenyl) sulfonamides, morpholinyl, piperidinyl, O—Z, CH$_2$—(CH$_2$)$_q$—Z, O—(CH$_2$)$_q$—Z, (CH$_2$)$_q$—O—Z, or CH=CH—Z;

wherein R$^1$ and R$^2$ are independently selected from ($C_1$–$C_6$)-straight or branched alkyl, ($C_2$–$C_6$)-straight or branched alkenyl or alkynyl, hydrogen or benzyl; or wherein R$_1$ and R$_2$ are taken together with the nitrogen atom to which they are bound to form a 5–7 membered heterocyclic ring;

Z is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and q is 0, 1 or 2;

X is N, O or CH;

when X is N or CH, Y is selected from hydrogen, Ar, ($C_1$–$C_6$)-straight or branched alkyl, ($C_2$–$C_6$)-straight or branched alkenyl or alkynyl, ($C_5$–$C_7$)-cycloalkyl-substituted-($C_1$–$C_6$)-straight or branched alkyl, ($C_5$–$C_7$) cycloalkyl-substituted-($C_2$–$C_6$)-straight or branched alkenyl or alkynyl, ($C_5$–$C_7$)-cycloalkenyl-substituted-($C_1$$C_6$)-straight or branched alkyl, ($C_5$–$C_7$)-cycloalkenylsubstituted-($C_2$–$C_6$)-straight or branched alkenyl of alkynyl, Ar-substituted-$(C_1-C_6)$-straight or branched alkyl, or Ar-substituted-$(C_2-C_6)$-straight or branched alkenyl or alkynyl;

when X is O, Y is a lone pair of electrons;

n is 0, 1 or 2;

m is 0, 1 or 2;

n+m is less than 4 and greater than 0;

the indicated ring in formulae II and IV is saturated, partially unsaturated or unsaturated;

1 to 2 carbon atoms in the ring in formulae II and IV are optionally replaced with a heteroatom independently selected from O, S, S(O), S(O)$_2$ or NR; and said ring in formula II and IV is optionally benzofused.

J is selected from hydrogen, $(C_1-C_6)$-straight or branched alkyl, $(C_2-C_6)$-straight or branched alkenyl or alkynyl, Ar-substituted-$(C_1-C_6)$-straight or branched alkyl, Ar-substituted-$(C_2-C_6)$-straight or branched alkenyl or alkynyl, or cyclohexylmethyl;

K is selected from $(C_1-C_6)$-straight or branched alkyl, Ar-substituted-$(C_1-C_6)$-straight or branched alkyl, $(C_2-C_6)$-straight or branched alkenyl or alkynyl, Ar-substituted-$(C_2-C_6)$-straight or branched alkenyl or alkynyl, or cyclohexylmethyl; wherein any one of the CH$_2$ groups of said alkyl, alkenyl or alkynyl chains in K is optionally replaced by O, S, S(O), S(O)$_2$ or N(R);

D is selected from is selected from Ar, $(C_1-C_6)$ straight or branched alkyl, $(C_2-C_6)$ straight or branched alkenyl or alkynyl, $(C_5-C_7)$ cycloalkyl substituted $(C_1-C_6)$ straight or branched alkyl, $(C_5-C_7)$ cycloalkyl substituted $(C_2-C_6)$ straight or branched alkenyl or alkynyl, $(C_5-C_7)$ cycloalkenyl substituted $(C_1-C_6)$ straight or branched alkyl, $(C_5-C_7)$ cycloalkenyl substituted $(C_2-C_6)$ straight or branched alkenyl of alkynyl, Ar-substituted $(C_1-C_6)$ straight or branched alkyl, or Ar-substituted $(C_2-C_6)$ straight or branched alkenyl or alkynyl;

wherein any one of the CH$_2$ groups of said alkyl chains in D other than the one that is directly bound to SO$_2$ in the compound, is optionally replaced by O, S, SO, SO$_2$ or NR.

R$^3$ is $(C_1-C_6)$-straight or branched alkyl, Ar-substituted-$(C_1-C_6)$-straight or branched alkyl, $(C_2-C_6)$-straight or branched alkenyl or alkynyl, or Ar-substituted-$(C_2-C_6)$-straight or branched alkenyl or alkynyl; wherein any one of the CH$_2$ groups of said alkyl, alkenyl or alkynyl chains in R$^3$ is optionally replaced by O, S, (O) S(O) S(O)$_2$ or N(R); and wherein any one of the CH$_2$ groups of said alkyl, alkenyl or alkynyl chains in R$^3$ except the CH$_2$ group bound to nitrogen, is optionally replaced with C(O), with the proviso that in formula II, when n is 0 and m is 1, the second CH$_2$ group in the alkyl chain of R$^3$ is not replaced with C(O).

The compositions disclosed herein comprise a compound of this invention, a carrier, and optionally, a neuronal growth factor.

The methods of stimulating nerve growth and preventing neurodegeneration disclosed herein employ the above compounds either alone or in combination with a neuronal growth factor. The methods are useful in treating or preventing nerve damage caused by various neurological diseases and physical traumas and also in ex vivo nerve regeneration.

DETAILED DESCRIPTION OF THE INVENTION

Applicants have discovered diverse genera of compounds with neuronal activity which do not bind to FKBP, and which do not have multi-drug resistance reversal activity. Without being bound by theory, applicants believe that the compounds disclosed in this application exert their neuronal activity by increasing cytoplasmic Ca$^{2+}$ concentrations. This is likely achieved by interaction, either direct or indirect, with a calcium release channel, such as the ryanodine receptor or the inositol 1,4,5-trisphosphate receptor, in the endoplasmic reticulum of the nerve cell.

Thus, according to one embodiment, the invention provides a method of stimulating nerve growth or preventing neurodegeneration by contacting nerve cells with a compound that:

a. increases cytoplasmic Ca$^{2+}$ concentration or binds to the ryanodine receptor;

b. does not bind to FKBP; and c. does not possess MDR reversal activity.

According to a related embodiment, the present invention provides a compound that:

a. has neuronal activity;

b. increases cytoplasmic Ca$^{2+}$ concentration or binds to the ryanodine receptor;

c. does not bind to FKBP; and d. does not possess MDR reversal activity.

The term "increases cytoplasmic Ca$^{2+}$ concentration", as used herein means a detectable increase in channel current recorded in the single channel recording assay described below in the presence of such a compound as compared to an appropriate control. Alternatively, the term "increases cytoplasmic Ca$^{2+}$ concentration", as used herein means a detectable shift in the fluorescence spectrum in the cell assay described herein.

The term "binds to the ryanodine receptor", as used herein, means that the compound specifically competes with ryanodine for binding to microsomes in the assay described below.

The term "does not bind FKBP", as used herein means that the compound demonstrates a Ki of 10 $\mu$M or greater in at least one of the rotamase inhibitory assays described below.

The term "does not possess MDR reversal activity", as used herein means that at a concentration of 2.5 $\mu$M, the compound has an MDR ratio of less than 7.0, and preferably less than 3.0 in at least one of the MDR assays described below.

Single-channel recording experiments are useful to determine if the compounds of this invention cause the requisite increase in cytoplasmic Ca$^{2+}$, concentration. These experiments are conducted as described in E. Kaftan et al., *Circulation Research*, 78, pp. 990–997 (1996), the disclosure of which is herein incorporated by reference. Single channel recordings are conducted under voltage clamp conditions with a pair of Ag/AgCl electrodes contacting the solutions via CsCl junctions. Vesicles are added to the cis chamber and fused with planar lipid bilayers composed of phosphatidylethanolamine/phosphatidylcholine (3:1, 30 mg/ml in decane, Avanti Polar Lipids). The trans chamber contains 250 mM HEPES and 53 mM Ba(OH)$_2$, pH 7.35; the cis chamber contains 250 mM HEPES-Tris pH 7.35. Compounds dissolved in methanol are added to the cis chamber. Channel currents are amplified using a bilayer clamp amplifier (BC-525A, Warner Instruments) and recorded on VHS tape (Dagen Corp.). Data are filtered to an eight-pole Bessel filter (Frequency Devices) to 500 Hz, digitized at 2 kHz, transferred to a personal computer, and analyzed with pClamp version 6.0 (Axon Instruments). Single channel recordings are done at least 3 times for each compound condition.

Ryanodine binding may be measured by incubating microsomal protein with $^3$H-ryanodine in buffer containing 36 mM Tris pH 7.2 and 50 mM KCl in the absence or presence of test compounds. Controls for maximum binding were done in the presence of 0.72 mM ATP and 36 μM $CaCl_2$. Nonspecific binding was measured in the presence of 25 μM unlabelled ryanodine. Binding reactions were incubated for 2 hours at room temperature, and then centrifuged for 15 minutes at 30,000×g. The pellets were solubilized and the radioactivity was measured by scintillation counting.

Alternatively, the flux of cytoplasmic $Ca^{2+}$ into the cell can be followed fluorescently. For example, neuronal cells can be incubated with NGF and a calcium binding fluorescent dye, such as Fura-2, in a calcium-containing buffer. Cells are imaged continuously both before and after the addition of a test compound of this invention. The difference in fluorescent intensity before and after the addition of compounds is then plotted as a ration of fluorescence units at 340 nm and 380 nm.

Testing a compound of this invention to confirm that it binds to FKBP12 with a Ki of 10 μM or higher may be achieved using several assays known in the art. In particular, those compounds may be assayed for their ability (or lack thereof) to inhibit rotamase. Examples of assays that measure inhibition of FKBP12 rotamase activity are those in which the isomerization of an artificial substrate—N-succinyl-Ala-Ala-Pro-Phe-p-nitroanilide—is followed spectrophotometrically [M. W. Harding et al., *Nature*, 341, pp. 758–60 (1989); by J. J. Siekierka et al., *Nature*, 341, pp. 755–57 (1989); and S. T. Park et al., *J. Biol. Chem.*, 267, pp. 3316–24 (1992)]. The assay includes the cis form of the substrate, FKBP12, the compound to be tested and chymotrypsin. Chymotrypsin is able to cleave p-nitroanilide from the trans form of the substrate, but not the cis form. Release of p-nitroanilide is measured.

Other FKBP binding assays include a competitive LH20 binding assay using labeled FK-506 as a reporting ligand. These have been described by M. W. Harding et al., *Nature*, 341, pp. 758–60 (1989) and by J. J. Siekierka et al., *Nature*, 341, pp. 755–57 (1989).

To determine whether a compound according to this invention has the requisite MDR ratio below 7.0, any of the assays described in U.S. Pat. Nos. 5,543,423, 5,717,092, 5,726,184 or 5,744,485, the disclosures of which are herein incorporated by reference, may be utilized.

In particular, cell lines which are known to be resistant to a particular drug are employed. These cell lines include, but are not limited to, the L1210, P388D, HL60 and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound ("MDR ratio").

According to one embodiment, the invention provides a compound of the formula:

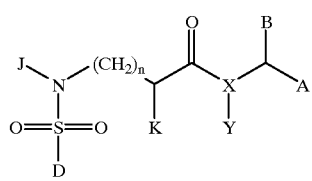

(I)

and pharmaceutically acceptable derivatives thereof wherein:

A and B are independently selected from hydrogen, Ar, ($C_1$–$C_6$)-straight or branched alkyl, ($C_2$–$C_6$)-straight or branched alkenyl or alkynyl, ($C_5$–$C_7$)-cycloalkyl substituted-($C_1$–$C_6$)-straight or branched alkyl, ($C_5$–$C_7$) cycloalkyl substituted-($C_2$–$C_6$)-straight or branched alkenyl or alkynyl, ($C_5$–$C_7$)-cycloalkenyl substituted-($C_1$–$C_6$)-straight or branched alkyl, ($C_5$–$C_7$)-cycloalkenyl substituted-($C_2$–$C_6$)-straight or branched alkenyl or alkynyl, Ar-substituted-($C_1$–$C_6$)-straight or branched alkyl, or Ar-substituted-($C_2$–$C_6$)-straight or branched alkenyl or alkynyl; wherein any one of the $CH_2$ groups of said alkyl, alkenyl or alkynyl chains in A or B is optionally replaced by O, S, S(O), $S(O)_2$ or N(R); wherein R is selected from hydrogen, ($C_1$–$C_6$)-straight or branched alkyl, or ($C_2$–$C_6$)-straight or branched alkenyl or alkynyl;

Ar is selected from phenyl, 1-naphthyl, 2-naphthyl, indenyl, azulenyl, fluorenyl, anthracenyl, 2-furyl, 3-furyl, 2-thienyl, 3-thienyl,2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isothiazolyl, 1,2,3-oxadiazolyl, 1,2,3-triazolyl, 1,3,4-thiadiazolyl, 1,2,4-triazolyl, 1,2,4-oxadiazolyl, 1,2,4-thiadiazolyl, 1,2,3-thiadiazolyl, benzoxazolyl, pyridazinyl, pyrimidinyl, pyrazinyl, 1,3,5-triazinyl, 1,3,5-trithianyl, indolizinyl, indolyl, isoindolyl, 3-Hindolyl, indolinyl, benzo[b]furanyl, benzot[b]thiophenyl, 1H-indazolyl, benzimidazolyl, benzthiazolyl, purinyl, 4H-quinolizinyl, quinolinyl, 1,2,3,4-tetrahydro-isoquinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl or other chemically feasible monocyclic, bicyclic or tricyclic ring systems, wherein each ring consists of 5 to 7 ring atoms and wherein each ring comprises 0 to 3 heteroatoms independently selected from N, N(R), O, S, S(O), or $S(O)_2$ and wherein each Ar is optionally substituted with one to three substituents independently selected from halogen, hydroxyl, nitro, —$SO_3H$, trifluoromethyl, trifluoromethoxy, ($C_1$–$C_6$)-straight or branched alkyl, ($C_2$–$C_6$)-straight or branched alkenyl, O-[($C_1$–$C_6$)-straight or branched alkyl], O-[($C_2$–$C_6$)-straight or branched alkenyl], O-benzyl, O-phenyl, 1,2-methylenedioxy, —N($R^1$)($R^2$), carboxyl, N-($C_1$–$C_5$-straight or branched alkyl or $C_2$–$C_5$-straight or branched alkenyl) carboxamides, N,N-di-($C_1$–$C_5$-straight or branched alkyl or $C_2$–$C_5$-straight or branched alkenyl) carboxamides, N-($C_1$–$C_5$-straight or branched alkyl or $C_2$–$C_5$-straight or branched alkenyl) sulfonamides, N,N-di-($C_1$–$C_5$-straight or branched alkyl or $C_2$–$C_5$-straight or branched alkenyl) sulfonamides, morpholinyl, piperidinyl, O—Z, $CH_2$—$(CH_2)_q$—Z, O—$(CH_2)_q$—Z, $(CH_2)_q$—Z—O—Z, or CH=CH—Z;

wherein $R^1$ and $R^2$ are independently selected from ($C_1$–$C_6$)-straight or branched alkyl, ($C_2$–$C_6$)-straight or branched alkenyl or alkynyl, hydrogen or benzyl; or wherein $R_1$ and $R_2$ are taken together with the nitrogen atom to which they are bound to form a 5–7 membered heterocyclic ring;

Z is selected from 4-methoxyphenyl, 2-pyridyl, 3-pyridyl, 4-pyridyl, pyrazyl, quinolyl, 3,5-dimethylisoxazoyl, isoxazolyl, 2-methylthiazoyl, thiazoyl, 2-thienyl, 3-thienyl, or pyrimidyl; and q is 0, 1 or 2;

X is N, O or C(R);

wherein when X is N or C(R), Y is selected from hydrogen, Ar, (C₁–C₆)-straight or branched alkyl, (C₂–C₆)-straight or branched alkenyl or alkynyl, (C₅–C₇)-cycloalkyl-substituted-(C₁–C₆)-straight or branched alkyl, (C₅–C₇)-cycloalkyl-substituted-(C₂–C₆)-straight or branched alkenyl or alkynyl, (C₅–C₇)-cycloalkenyl-substituted-(C₁–C₆)-straight or branched alkyl, (C₅–C₇)-cycloalkenylsubstituted-(C₂–C₆)-straight or branched alkenyl of alkynyl, Ar-substituted-(C₁–C₆)-straight or branched alkyl, or Ar-substituted-(C₂–C₆)-straight or branched alkenyl or alkynyl;

when X is 0, Y is a lone pair of electrons;

K is selected from (C₁–C₆)-straight or branched alkyl, Ar-substituted-(C₁–C₆)-straight or branched alkyl, (C₂–C₆)-straight or branched alkenyl or alkynyl, Ar-substituted-(C₂-c₆)-straight or branched alkenyl or alkynyl, or cyclohexylmethyl; wherein any one of the CH₂ groups of said alkyl, alkenyl or alkynyl chains in K is optionally replaced by O, S, S(O), S(O)₂ or N(R)

n is 0, 1 or 2;

J is selected from hydrogen, (C₁–C₆)-straight or branched alkyl, (C₂–C₆)-straight or branched alkenyl or alkynyl, Ar-substituted-(C₁–C₆)-straight or branched alkyl, Ar-substituted-(C₂–C₆)-straight or branched alkenyl or alkynyl, or cyclohexylmethyl; and D is selected from is selected from Ar, (C₁–C₆) straight or branched alkyl, (C₂–C₆) straight or branched alkenyl or alkynyl, (C₅–C₇) cycloalkyl substituted (C₂–C₆) straight or branched alkyl, (C₅–C₇) cycloalkyl substituted (C₂–C₆) straight or branched alkenyl or alkynyl, (C₅–C₇) cycloalkenyl substituted (C₁–C₆) straight or branched alkyl, (C₅–C₇) cycloalkenyl substituted (C₂–C₆) straight or branched alkenyl of alkynyl, Ar-substituted (C₁–C₆)-straight or branched alkyl, or Ar-substituted (C₂–C₆) -straight or branched alkenyl or alkynyl; wherein any one of the CH₂ groups of said alkyl chains in D other than the one that is directly bound to SO₂ in the compound, is optionally replaced by O, S, SO, SO₂ or NR.

In one preferred embodiment of formula I, A and B are not simultaneously hydrogen. Even more preferred is when at least one of A or B is a (C₁–C₆)-straight alkyl terminally substituted with Ar (which itself is substituted or unsubstituted). More preferably, at least one of A or B is a (C₁–C₆)-straight alkyl terminally substituted with pyridine (which itself substituted or unsubstituted).

According to another preferred embodiment of formula I, X is nitrogen or oxygen. In another preferred embodiment of formula I, J is a (C₁–C₃)-straight alkyl.

In yet another preferred embodiment of formula I, K is an Ar-substituted (C₁–C₃)-straight alkyl. More preferred is when K is a (C₁–C₃)-straight alkyl terminally substituted with an unsubstituted phenyl.

According to another preferred embodiment of formula I, D is is selected from (C₁–C₆) straight or branched alkyl, Ar, Ar-substituted (C₁–C₆) straight or branched alkyl, Ar-substituted (C₂–C₆) straight or branched alkenyl or alkynyl, or —CH₂—S(O)₂—(C₁–C₄) straight or branched alkyl.

More preferably, D is selected from aminophenyl, nitrophenyl, isopropyl, benzyl, fluorophenyl, cyanophenyl, methoxyphenyl, dimethoxyphenyl, methylsulfonylmethyl, ethylenephenyl, dinitroanilinophenyl, N,N-dimethylaminophenylazophenyl N,N-dimethyl- aminonaphthyl or acetamidophenyl.

Most preferably, D is selected from 4-aminophenyl, 2-nitrophenyl, methylsulfonylmethyl, benzyl, ethylenephenyl, 4-fluorophenyl, 4-cyanophenyl, 3,4-dimethoxyphenyl, 4-methoxyphenyl, 4-(2,4-dinitroanilino) phenyl, 4-((4-(N,N-dimethylamino) phenyl)azo)phenyl, 5-(N,N-dimethylamino)naphthyl or 4-acetamidophenyl.

According to another preferred embodiment, Y is methyl.

In another preferred embodiment, n is 0.

According to another embodiment, the invention provides a compound of the formula:

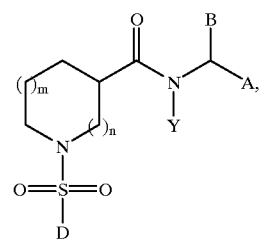

(II)

and pharmaceutically acceptable derivatives thereof, wherein A, B, Y, D, n and subcomponents thereof are as defined above;

m is 0, 1 or 2;

n+m is less than 4 and greater than 0;

the indicated ring in formula II is saturated, partially unsaturated or unsaturated;

1 to 2 carbon atoms in the ring in formula II are optionally replaced with a heteroatom independently selected from O, S, S(O), S(O)₂ or NR; and said ring in formula II is optionally benzofused.

Preferably, in formula II, n is 0, m is 2 and the ring is fully saturated.

According to another preferred embodiment of formula II one carbon in said ring is optionally replaced with a heteroatom selected from O, S, SO or SO₂.

Preferred embodiments for the individual components in the compounds of formula II are the same as those set forth above for compounds of formula I. The most preferred compounds of formula I and II are set forth in Tables 1 and 2, below:

TABLE 1

Compounds of formula I.

| Cmpd # | Structure |
|---|---|
| 2 | ![structure] |

TABLE 1-continued
Compounds of formula I.
| Cmpd # | Structure |
|---|---|
| 4 | 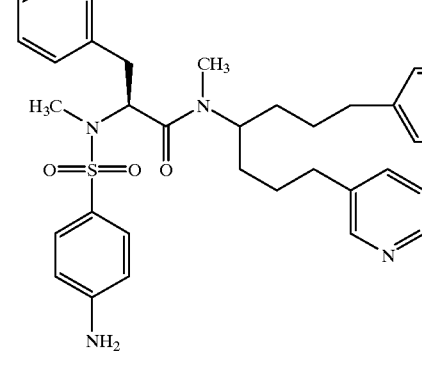 |
| 5 | 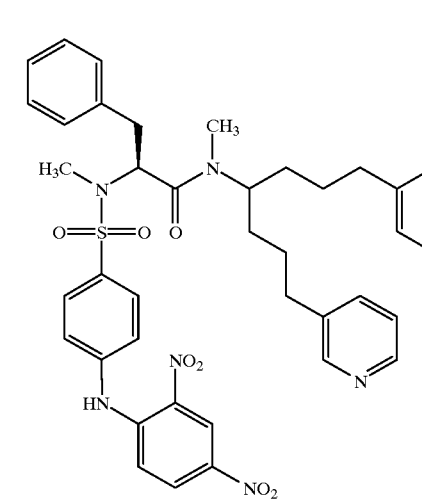 |
| 6 | 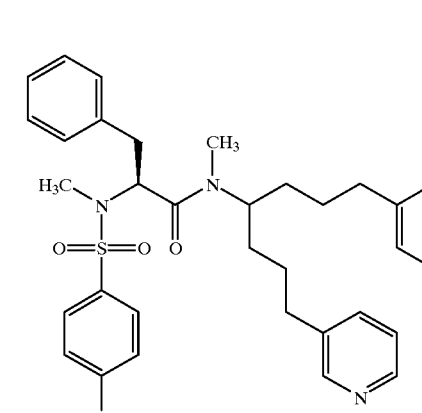 |
| 7 | 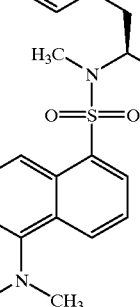 |
| 8 | 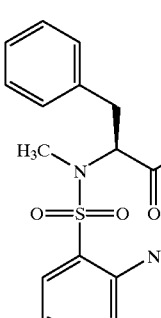 |
| 11 | 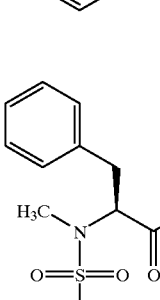 |
| 12 | 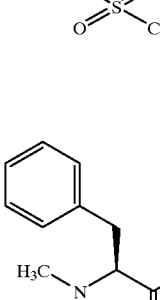 |

TABLE 1-continued

Compounds of formula I.

| Cmpd # | Structure |
|---|---|
| 13 | 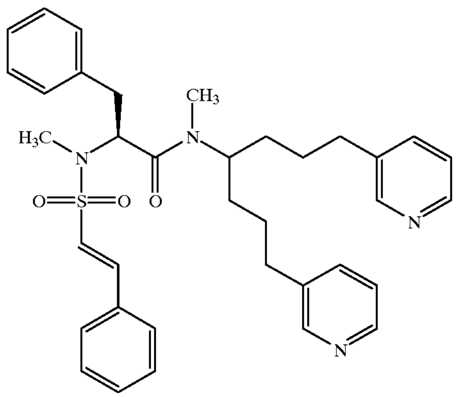 |
| 14 | 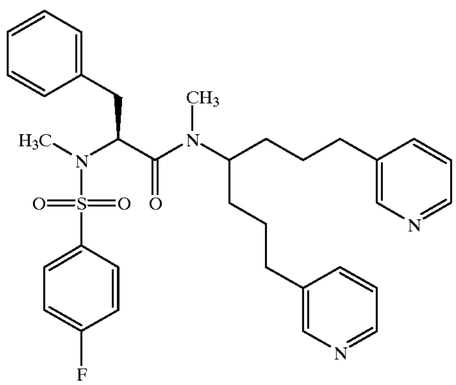 |
| 15 | 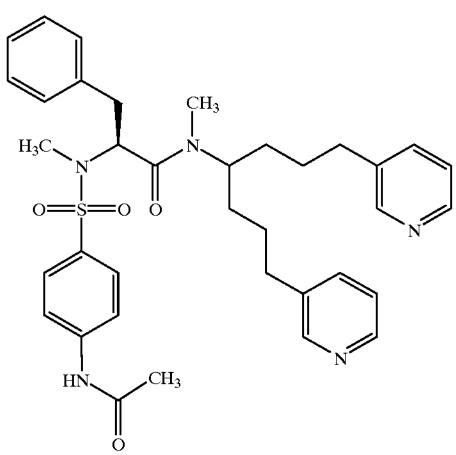 |
| 16 | |
| 17 | |
| 18 | |

TABLE 2

Compounds of formula II

| Cmpd # | Structure |
|---|---|
| 1 | 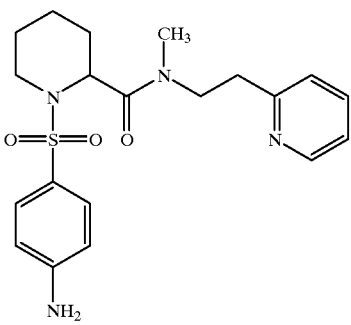 |
| 3 | 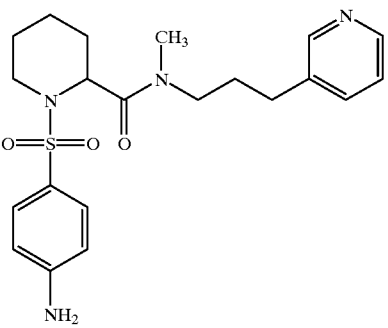 |

According to another embodiment of this invention is provided a compound of the formula:

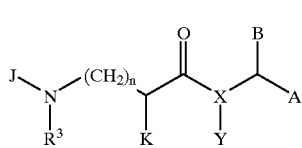

(III)

and pharmaceutically acceptable derivatives thereof, wherein:

A, B, X, Y, K, J, n and subcomponents thereof are as defined above for compounds of formula I; and $R^3$ is $(C_1-C_6)$-straight or branched alkyl, Ar-substituted-$(C_1-C_6)$-straight or branched alkyl, $(C_2-C_6)$-straight or branched alkenyl or alkynyl, or Ar-substituted-$(C_2-C_6)$-straight or branched alkenyl or alkynyl; wherein any one of the $CH_2$ groups of said alkyl, alkenyl or alkynyl chains in $R^3$ is optionally replaced by O, S, S(O), S(O)$_2$ or N(R); and wherein any one of the $CH_2$ groups of said alkyl, alkenyl or alkynyl in $R^3$ except the $CH_2$ group bound to nitrogen, is optionally replaced with C(O).

According to another embodiment, the invention provides a compound of the formula:

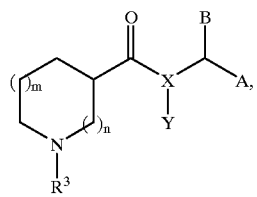

(IV)

and pharmaceutically acceptable derivatives thereof; wherein:

A, B, X, Y, n, m and subcomponents thereof are as defined for compounds of formula (II); and $R^3$ is as defined for compounds of formula (III), with the proviso that in formula IV, when n is 0 and m is 1, the second $CH_2$ group in the alkyl, alkenyl or alkynyl chain of $R^3$ is not replaced with C(O).

The term "second $CH_2$ group in the alkyl chain of $R^3$" refers to the $CH_2$ group bound immediately to the $CH_2$ group that is bound to nitrogen (indicated in bold in the formula below:

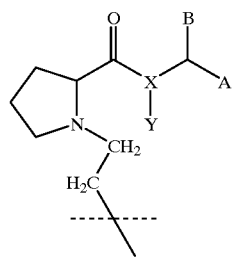

Preferably, in the compounds of formulae III and IV, at least one of A or B is Ar-substituted $(C_1-C_6)$ alkyl chain. Even more preferred is when at least one of A or B is is a $(C_1-C_6)$-alkyl chain terminally substituted with phenyl or pyridinyl.

According to another preferred embodiment in the compounds of formulae III or IV, X is N or O.

According to yet another preferred embodiment, in the compounds of formula III, K is an Ar-substituted alkyl, alkenyl or alkynyl. More preferably, K is benzyl.

According to another preferred embodiment, in compounds of formula III, J is hydrogen or alkyl, preferably methyl.

In compounds of formulae III and IV, $R^3$ is preferably hydrogen, $(C_1-C_6)$-alkyl, $(C_1-C_6)$-alkyl terminally substituted with pyridyl, or 3,4,5-trimethyoxybenzoylmethyl.

In a preferred embodiment of formula III, n is 0.

In a preferred embodiment the indicated ring in formula IV is fully saturated.

In another preferred embodiment of the compounds of formula IV, m+n is 1 or 2. Even more preferred is when n is 0 and m is 1 or 2. Most preferably, n is 0 and m is 2.

The most preferred compounds of formulae III and IV are listed in the table below, as well as being described in the examples:

TABLE 3

Compounds of formulae III and IV.

| Cmpd # | Structure |
| --- | --- |
| 101 | (2-piperidinecarboxylic acid benzyl ester) |
| 102 | (piperidine-2-carboxylic acid 1,5-bis(pyridin-3-yl)pentan-3-yl ester) |
| 103 | (piperidine-2-carboxylic acid (pyridin-3-ylmethyl)amide) |
| 104 | (piperidine-2-carboxylic acid (pyridin-4-ylmethyl)amide) |
| 105 | (1-[2-(3,4,5-trimethoxyphenyl)-2-oxoethyl]piperidine-2-carboxylic acid 1,5-bis(pyridin-3-yl)pentan-3-yl ester) |
| 106 | (piperidine-2-carboxylic acid N-methyl-N-[2-(pyridin-2-yl)ethyl]amide) |
| 107 | (2-(methylamino)-3-phenyl-N-methyl-N-[2-(pyridin-2-yl)ethyl]propanamide) |
| 108 | (2-(methylamino)-3-phenyl-N-methyl-N-[3-(pyridin-3-yl)propyl]propanamide) |
| 109 | (2-(methylamino)-3-phenyl-N-R$_3$-N-[1,5-bis(pyridin-3-yl)pentan-3-yl]propanamide) |
| 110 | (piperidine-2-carboxylic acid N-methyl-N-[3-(pyridin-3-yl)propyl]amide) |
| 111 | (1-methylpiperidine-2-carboxylic acid 1-[3-(pyridin-4-yl)propyl]-4-(pyridin-3-yl)butyl ester) |

TABLE 3-continued

Compounds of formulae III and IV.

| Cmpd # | Structure |
| --- | --- |
| 112 | 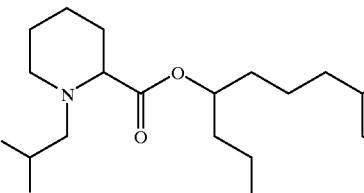 |
| 113 | 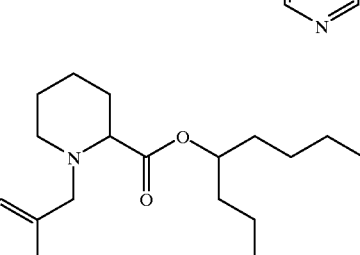 |

This invention includes all optical and racemic isomers of the compounds of formulae I through IV, as well as pharmaceutically acceptable derivatives thereof.

A "pharmaceutically acceptable derivative," as used herein denotes any pharmaceutically acceptable salt, ester, prodrug, or salt of such ester or prodrug, of a compound of this invention or any other compound which, upon administration to a patient, is capable of providing (directly or indirectly) a compound of this invention, or a metabolite or residue thereof, characterized by neuronal activity.

Surprisingly and unexpectedly, the compounds of formulae (I) through (IV) of this invention do not bind FKBP, do not inhibit its rotamase activity and are not immunosuppressive. Moreover, although the compounds of this invention bear some structural resemblance to compounds which are known to reverse multi-drug resistance (see U.S. Pat. No. 5,543,423, WO 95/26337 and WO 94/07858), the present compounds appear to have no activity against MDR. Thus, the presently disclosed compounds advantageously possess neuronal activity, without interfering with other pathways known to be affected by structurally similar compounds.

The nerve growth activity of the compounds of this invention may be initially assayed using several cell culture assays known in the art. For example, the compounds of this invention may be tested in a neurite outgrowth assay using pheochromocytoma PC12 cells as described by Lyons et al., *PNAS*, 91, pp. 3191–3195 (1994). A similar assay may be carried out in SH-SY5Y human neuroblastoma cells. Alternatively, the chick dorsal root ganglia assay described in U.S. Pat. No. 5,614,547 or in G. S. Hamilton et al., *Bioorg. Med. Chem. Lett.*, (1997) and references cited therein, may be utilized.

The compounds of this invention may also be assayed for nerve growth activity in vivo using a mouse model of Parkinson's disease [J. P. Steiner et al., *Proc. Natl. Acad. Sci. USA*, 94, pp. 2019–23 (1997), U.S. Pat. No. 5,721,256] or following surgical sciatic nerve crush in rats.

According to another embodiment, the invention provides compositions comprising a compound of any of formula (I) through (IV) and a pharmaceutically acceptable carrier. Preferably, the compositions of this invention are formulated for administration to a mammal (i.e., pharmaceutical compositions).

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and N-($C_{1-4}$ alkyl)$_{4+}$ salts.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these pharmaceutical compositions include, but are not limited to, ion exchangers, alumina, aluminum stearate, lecithin, self-emulsifying drug delivery systems (SEDDS) such as da-tocopherol, polyethyleneglycol 1000 succinate, or TPGS, surfactants used in pharmaceutical dosage forms such as Tweens or other similar polymeric delivery matrices, serum proteins, such as human serum albumin, gelatin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polylactic acid, ployaceticpolyglycollic acid, citric acid, cellulose-based substances, such as HPC and HPMC, polyethylene glycol, sodium carboxymethylcellulose, polyacrylates, waxes, polyethylene-polyoxypropylene-block polymers, polyethylene glycol, wool fat. Cyclodextrins such as α-, β-, and Δ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the compounds of this invention.

According to another embodiment, the pharmaceutical compositions of this invention additionally comprise a neurotrophic factor. The term "neurotrophic factor", as used herein, refers to compounds which are capable of stimulating growth or proliferation of nervous tissue. As used in this application, the term "neurotrophic factor" excludes the compounds described herein.

Numerous neurotrophic factors have been identified in the art and any of those factors may be utilized in the compositions of this invention. These neurotrophic factors include, but are not limited to, nerve growth factor (NGF), insulin growth factor (IGF-1) and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3), neurotrophin 4/5 (NT-4/5), or any of the compounds described in Wo 97/36869, WO 96/41609, WO 97/16190, WO 96/40633, WO 97/18828, WO 96/40140 or WO 98/13355. The most preferred neurotrophic factor in the compositions of this invention is NGF.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose, corn starch, dicalcium phosphate and microcrystalline cellulose (Avicel). Lubricating agents, such as magnesium stearate and talc, are also typically added. For oral administration in a capsule form, useful diluents include lactose, dried corn starch and TPGS, as well as the other diluents used in tablets. For oral administration in a soft gelatin capsule form (filled with either a suspension or a solution of a compound of this invention), useful diluents include PEG400, TPGS, propylene glycol, Labrasol, Gelucire, Transcutol, PVP and potassium acetate. When aqueous suspensions are administered orally, the active ingredient is combined with emulsifying and suspending agents, such as sodium CMC, methyl cellulose, pectin and gelatin. If desired, certain sweetening and/or flavoring and/or coloring agents may be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax, gelatin, glycerin and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, stearic acid, cetyl stearate, cetyl alcohol, lanolin, magnesium hydroxide, kaolin and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both, the compound and the neurotrophic factor (in those compositions which comprise a neurotrophic factor) that may be combined with the carrier materials to produce a single dosage form will vary depending upon the host treated, the particular mode of administration. Preferably, the compositions of this invention should be formulated so that a dosage of between 0.01–10 mg/kg body weight/day of a compound of this invention can be administered. More preferably, the dosage is between 0.1–10 mg/kg body weight/day.

In those compositions which comprise a neurotrophic factor, that factor and the compounds of this invention act synergistically to stimulate neurite outgrowth or prevent neurodegeneration. Therefore, the amount of neurotrophic factor in such compositions will be less than that required in a monotherapy utilizing only that factor. In such compositions a dosage of between 0.01–10 mg/kg body weight/day of the neurotrophic factor can be administered.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and neurotrophic factor in the composition.

According to another embodiment, this invention provides methods for stimulating neurite outgrowth and nerve growth and for preventing neurodegeneration. In one aspect of this embodiment, the method is used to stimulate neurite outgrowth and nerve growth and prevent neurodegeneration in a patient and is achieved by administering to the patient a pharmaceutically acceptable composition comprising any of the compounds of this invention and a pharmaceutically acceptable carrier. The amount of compound utilized in these methods is between about 0.01 and 10 mg/kg body weight/day.

This method may be used to treat nerve damage and prevent neurodegeneration caused by a wide variety of diseases or physical traumas. These include, but are not limited to, trigeminal neuralgia, glossopharyngeal neuralgia, Bell's Palsy, myasthenia gravis, muscular dystrophy, muscle injury, progressive muscular atrophy, progressive bulbar inherited muscular atrophy, herniated, ruptured or prolapsed invertebrae disk syndrome's, cervical spondylosis, plexus disorders, thoracic outlet destruction syndromes, peripheral neuropathies, such as those caused by lead, dapsone, ticks, or porphyria, other peripheral myelin disorders, Alzheimer's disease, Gullain-Barre syndrome, Parkinson's disease and other Parkinsonian disorders, ALS, multiple sclerosis, other central myelin disorders, stroke and ischemia associated with stroke, neural paropathy, other neural degenerative diseases, motor neuron diseases, sciatic crush, neuropathy associated with diabetes, spinal cord injuries, facial nerve crush and other trauma, chemotherapy- and other medication-induced neuropathies and Huntington's disease.

In another aspect of this embodiment, the method is used to stimulate nerve growth ex vivo. For this aspect, the compounds or compositions described above can be applied directly to the nerve cells in culture. This aspect of the invention is useful for ex vivo nerve regeneration.

According to an alternate embodiment, the method of stimulating neurite outgrowth or preventing neurodegeneration comprises the additional step of treating a patient or ex vivo nerve cells in culture with a neurotrophic factor, such as those contained in the compositions of this invention described above. This embodiment includes administering the compound and the neurotrophic agent in a single dosage form or in separate, multiple dosage forms when they are to be administered to a patient. If separate dosage forms are utilized, they may be administered concurrently, consecutively or within less than about 5 hours of one another.

In order that the invention described herein may be more fully understood, the following examples are set forth. It should be understood that these examples are for illustrative purposes only and are not to be construed as limiting this invention in any manner.

General Methods

Proton nuclear magnetic resonance ($^1$H NMR) spectra were recorded at 500 MHz on a Bruker AMX 500. Chemical shifts are reported in parts per million relative to Me$_4$Si. Analytical high performance liquid chromatography was performed on a Hewlett-Packard 1050 liquid chromatograph.

EXAMPLE 1

N-(4-Aminobenzenesulfonamido)-(S)-Piperidine-2-Carboxylic Acid-2-((N Methyl)-2-Pyridylethyl) Amide The synthesis of N-(4-aminobenzenesulfonamido)-(S)-piperidine-2-carboxylic acid-2-((N-methyl)-2-pyridylethyl) amide (compound 1) is set forth below.

A. (S)-Piperidine-1,2-Dicarboxylic Acid-1-(Tert-Butyl ester)-2-((N Methyl)-2-Pyridinylethyl) Amide.

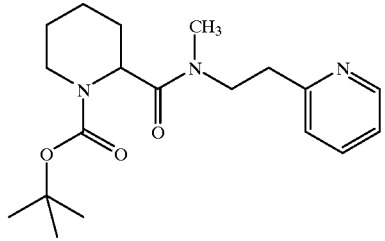

To a solution of (S)-piperidine-1,2 dicarboxylic acid 1-tert-butylester (5.0 g, 21.8 mmol) in methylene chloride (50 ml) was added EDC (6.0 g, 191.71, 31.2 mmol) followed by the addition of 2-(2-methylaminoethyl)pyridine (3.0 g, 22 mmol) The mixture was allowed to stir at ambient temperature for 24 hours.

The solution was diluted with 200 ml ethyl acetate and water (50 ml). The aqueous layer made basic by the addition of 2N NaOH until pH 12–13 was achieved. The separated organics were dried over anhydrous MgSO$_4$ and concentrated under reduced pressure. The crude product was purified via medium pressure liquid chromatography using a gradient solvent system of 1:99 methanol/methylene chloride followed by 2:98 methanol/methylene chloride solution to give 3.8 g (50% yield) of the title compound as a colorless oil. TLC: Rf=0.49 (5:95 methanol/methylene chloride), [$^1$H]-NMR (CDCl$_3$) consistent with structure.

B. (S)-Piperidine-2-Carboxylic Acid-2-((N Methyl)-2-Pyridylethyl) Amide.

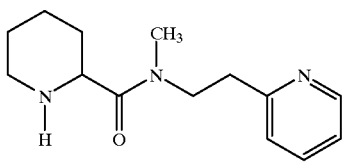

To the compound of part A (3.8 g, 10.9 mmol) in methylene chloride (25 ml) was added trifluoroacetic acid (10 ml, 130 mmol). The mixture was allowed to stir 2 hours at ambient temperature. The solution was concentrated under reduced pressure to dryness. The residue was taken up in ethyl acetate (200 ml) and water (50 ml). The aqueous layer was made basic by the addition of 2N NaOH until pH 14–15 was achieved.

The separated organics were dried over anhydrous MgSO$_4$ and concentrated under reduced pressure. The crude product was purified via medium pressure liquid chromatography using a gradient solvent system of 1:99 methanol/methylene chloride followed by 1:10:90 NH$_4$OH/methanol/methylene chloride to give 2.2 g (81% yield) of the title compound as a colorless oil. TLC: Rf=0.11 (1:10:90 NH$_4$OH/methanol/methylene chloride), HPLC: Rt=5.22 min, [$^1$H]—NMR (CDCl$_3$) consistent with structure.

C. N-(4-Nitrobenzenesulfonamido)-(S)-Piperidine-2-Carboxylic Acid-2-((N Methyl)-2-Pyridylethyl) Amide.

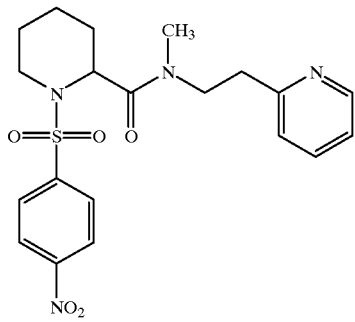

To a solution of the compound of part B (200 mg, 0.81 mmol) in methylene chloride (5 ml) was added triethylamine (2.0 ml, 101.19, 19.8 mmol) followed by the addition of 4-nitrobenzenesulfonylchloride (260 mg, 1.22 mmol). The mixture was allowed to stir at ambient temperature for 24 hours. The solution was diluted with 100 ml ethyl acetate and a saturated solution of sodium bicarbonate (50 ml). The separated organics were dried over anhydrous MgSO$_4$ and concentrated under reduced pressure. The crude product was purified via medium pressure liquid chromatography using a gradient solvent system of methylene chloride followed by 1:99 methanol/methylene chloride solution to give 273 mg (78% yield) of the title compound as an yellowish oil. TLC: Rf=0.57 (5:95 methanol/methylene chloride), [$^1$H]-NMR (CDCl$_3$) onsistent with structure.

D. N-(4-aminobenzenesulfonamido)-(S)-piperidine-2-carboxylic acid-2-((N-methyl)-2-pyridylethyl) amide (compound 1).

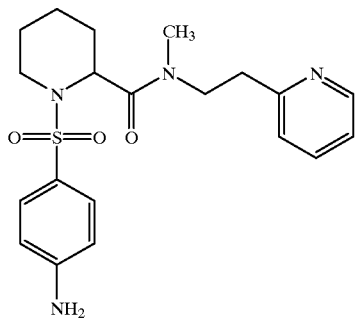

A solution of the compound from step C (273 mg, 0.63 mmol) in ethyl acetate (10 ml) and ethanol (10 ml) was treated under ambient temperature with 150 mg of 10% palladium on carbon and hydrogenated for 24 hours under a slight positive pressure of hydrogen. The mixture was filtered and concentrated in vacuo and the crude product purified via medium pressure liquid chromatography using methylene chloride followed by 2:98 methanol/methylene chloride followed by 0.5:5:95 NH$_4$OH/methanol/methylene chloride solution as the solvent system to give 102 mg (40% yield) of the title compound as a yellowish oil. TLC: Rf=0.36 (1:10:90 NH$_4$OH/methanol/methylene chloride), HPLC: Rt=6.86 min, [$^1$H]-NMR (CDCl$_3$) consistent with structure.

EXAMPLE 2

(S)-(N-Methyl)-2-(Methyl-(4-Amino-Benzenesulfanilamido))-3-Phenyl-N-(2-(Pyridin-2yl) Ethyl) Propionamide The synthesis of (S)-(N-methyl)-2-(methyl-(4-amino-benzenesulfanilamido))-3-phenyl-N-(2-(pyridin-2yl) ethyl) propionamide (compound 2) is set forth below.

A. (N-Methyl)-2-(Methyl-2-(Tertbutyloxycarbonyl) Amino-3-Phenyl-N-(3-Pyridin-4-yl)-Propylbutyl Propionamide.

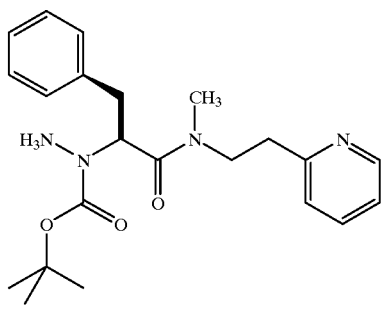

To a solution of Boc-(N-Methyl)phenylalanine (5.0 g, 17.8 mmol) in methylene chloride (50 ml) was added EDC (6.0 g, 191.71, 31.2 mmol) followed by the addition of 2-(2-methylaminoethyl)pyridine (2.5 g, 18.4 mmol). The mixture was allowed to stir at ambient temperature for 24 hours. The solution was diluted with 200 ml ethyl acetate and water (50 ml). The aqueous layer was made basic by the addition of 2N NaOH until pH 12 was achieved. The separated organics were dried over anhydrous MgSO$_4$ and concentrated under reduced pressure. The crude product was purified via medium pressure liquid chromatography using a gradient solvent system of 1:99 methanol/methylene chloride followed by 2:98 methanol/methylene chloride solution to give 2.83 g (40% yield) of the title compound as a colorless oil. TLC: Rf=0.56 (5:95 methanol/ methylene chloride), [¹H]-NMR (CDCl₃) consistent with structure.

B. (N-methyl)-2-(methylamino)-3-phenyl-N-(2(pyridin-2-yl)ethyl) propionamide.

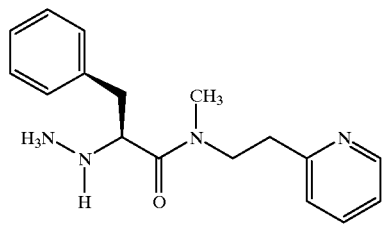

To the compound of step A (2.83 g, 7.1 mmol) in methylene chloride (25 ml) was added trifluoroacetic acid (10 ml, 130 mmol). The mixture was allowed to stir 2 hours at ambient temperature. The solution was concentrated under reduced pressure to dryness. The residue was taken up in ethyl acetate (200 ml) and water (50 ml). The aqueous layer was made basic by the addition of 2N NaOH until pH 14–15 was achieved.

The separated organics were dried over anhydrous MgSO₄ and concentrated under reduced pressure. The crude product was purified via medium pressure liquid chromatography using a gradient solvent system of 1:99 methanol/methylene chloride followed by 1:10:90 NH₄OH/methanol/methylene chloride) to give 1.53 g (75% yield) of the title compound as a colorless oil. TLC: Rf=0.70 (1:10:90 NH₄OH/methanol/methylene chloride). HPLC: Rt=5.54 min, [¹H]-NMR (CDCl₃) consistent with structure.

C. (S)-(N-methyl)-2-(methyl-(4-nitrobenzenesulfanilamido))-3-phenyl-N-(2-(pyridin-2-yl) Ethyl) propionamide.

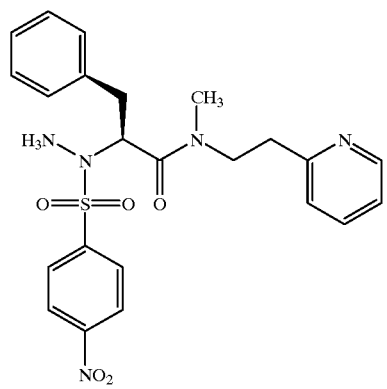

To a solution of the compound of step B (300 mg, 1.05 mmol) in methylene chloride (15 ml) was added triethylamine (2.0 ml, 101.19, 19.8 mmol) followed by the addition of 4-nitrobenzenesulfonylchloride (330 mg, 1.56 mmol). The mixture was allowed to stir at ambient temperature for 24 hours. The solution was diluted with 100 ml ethyl acetate and a saturated solution of sodium bicarbonate (50 ml). The separated organics were dried over anhydrous MgSO₄ and concentrated under reduced pressure. The crude product was purified via medium pressure liquid chromatography using a gradient solvent system of methylene chloride followed by 1:99 methanol/methylene chloride solution to give 453 mg (89% yield) of the title compound as a yellowish oil. TLC: Rf=0.63 (5:95 methanol/methylene chloride), [¹H]-NMR (CDCl₃) consistent with structure.

D. (S)-(N-methyl)-2-(methyl-(4-aminobenzenesulfanilamido))-3-phenyl-N-(2-(pyridin-2-yl) ethyl) propionamide (compound 2).

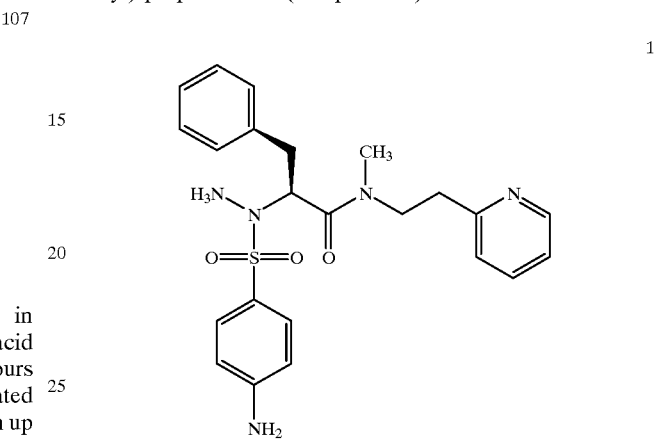

A solution of the compound from step C (453 mg, 0.94 mmol) in ethyl acetate (20 ml) was treated under ambient temperature with 150 mg of 10% palladium on carbon and hydrogenated for 24 hours under a slight positive pressure of hydrogen. The mixture was filtered and concentrated in vacuo and the crude product purified via medium pressure liquid chromatography using 2:98 methanol/methylene chloride followed by 0.5:5:95 NH₄OH/methanol/methylene chloride solution as the solvent system to give 194 mg (46% yield) of the title compound as a yellowish oil. TLC: Rf=0.46 (1:10:90 NH₄OH/methanol/methylene chloride), HPLC: Rt=9.04 min, [¹H]NMR (CDCl₃) consistent with structure.

EXAMPLE 3

N-(4-Nitrobenzenesulfonamido)-(S)-Piperidine-2-Carboxylic Acid-(N Methyl)-3-(Pyridin-3-Yl) Propyl) Amide The synthesis of N-(4-nitrobenzenesulfonamido)(S)-piperidine-2-carboxylic acid-((N-methyl)-3-(pyridin-3-yl) propyl) amide (compound 3) is described below.

A. 3-(3-Bromopropyl)-Pyridine.

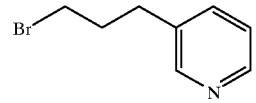

To a solution of 3-pyridinepropanol (9.50 g, 69.3 mmol) in DMF (50 ml) was added triphenylphosphine (20.0 g, 76.2 mmol) followed by the addition of bromine (5.4 ml, 104 mmol). The mixture was allowed to stir at ambient temperature for 48 hours. The solution was diluted with 200 ml water and the aqueous layer made basic by the addition of 2N NaOH until pH 12–13 was achieved. The organics were taken up in ethyl acetate (200 ml). The separated organics were dried over anhydrous MgSO₄ and concentrated under reduced pressure. The crude product was purified via medium pressure liquid chromatography using a gradient solvent system of methylene chloride followed by a 1:99 methanoll methylene chloride solution to give 11.8 g (85% yield) of the title compound as an yellowish orange oil. TLC: Rf=0.8 (3:97 methanol/methylene chloride), [¹H]-NMR (CDCl₃) consistent with structure.

B. N-Methyl-3-(3-Aminopropyl)-Pyridine.

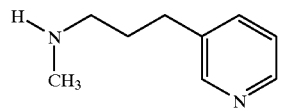

A solution of the compound from step A (11.8 g, 59 mmol) in methanol (50 ml) was bubbled N-methylamine gas for a period of 10 to 15 min until saturated. The flask was sealed and the mixture allowed to stir overnight at ambient temperature. The mixture was concentrated in vacuo and the residue taken up in ethyl acetate and water. The aqueous layer was made basic by the addition of 2N NaOH until pH 14–15 was achieved. The organics were taken up in ethyl acetate (250 ml). The separated organics were dried over anhydrous MgSO₄ and concentrated under reduced pressure. The crude product purified via medium pressure liquid chromatography using methylene chloride followed by 5:95 methanol/methylene chloride followed by a 1:10:90 NH₄OH/methanol/methylene chloride solution as the solvent system to give 3.2 g (36% yield) of the title compound as colorless oil. TLC: Rf=0.14 (1:10:90 NH₄OH/methanol/methylene chloride), [¹H]-NMR (CDCl₃) consistent with structure.

C. N-methyl-(S)-piperidine-1,2-dicarboxylic acid-1-(tert-butyl ester)-3-((pyridin-3-yl)propyl) amide.

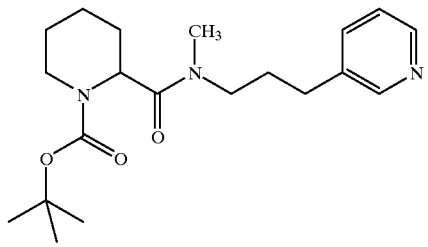

To a solution of (S)-piperidine-1,2 dicarboxylic acid 1-tert-butylester (2.28 g, 9.9 mmol) in methylene chloride (30 ml) was added EDC (2.0 g, 191.71, 10.4 mmol) followed by the compound from step B (11.8 g, 59 mmol). The mixture was allowed to stir at ambient temperature for 24 hours. The solution was diluted with 200 ml ethyl acetate and a saturated solution of sodium bicarbonate (50 ml). The separated organics were dried over anhydrous MgSO₄ and concentrated under reduced pressure.

The crude product was purified via medium pressure liquid chromatography using a gradient solvent system of 1:99 methanol/methylene chloride followed by 5:95 methanol/methylene chloride solution to give 1.2 g (33% yield) of the title compound as a colorless oil. TLC: Rf=0.28 (5:95 methanol/methylene chloride), [¹H]NMR (CDCl₃) consistent with structure.

D. (S)-piperidine-2-carboxylic acid-((N-methyl)-3-(pyridin-3-yl)propyl) amide.

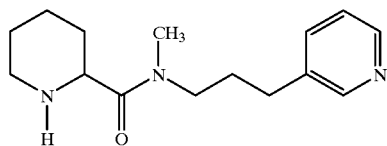

To the compound from step C (1.2 g, 3.3 mmol) in methylene chloride (20 mL) was added trifluoroacetic acid (10 ml, 130 mmol). The mixture was allowed to stir 3 hours at ambient temperature. The solution was concentrated under reduced pressure to dryness. The residue was taken up in ethyl acetate (200 ml) and 2N NaOH (50 ml). The separated organics were dried over anhydrous MgSO₄ and concentrated under reduced pressure.

The crude product was purified via medium pressure liquid chromatography using a gradient solvent system of 5:95 methanol/methylene chloride followed by 1:10:90 NH₄OH/methanol/methylene chloride) to give 850 mg (98% yield) of the title compound as a colorless oil. TLC: Rf=0.17 (1:10:90 NH₄OH/methanol/methylene chloride)., HPLC: Rt=6.67 min, [¹H]-NMR (CDCl₃) consistent with structure.

E. N-(4-nitrobenzenesulfonamido)-(S)-piperidine-2-carboxylic acid-((N-methyl)-3-(pyridin-3-yl)propyl) amide.

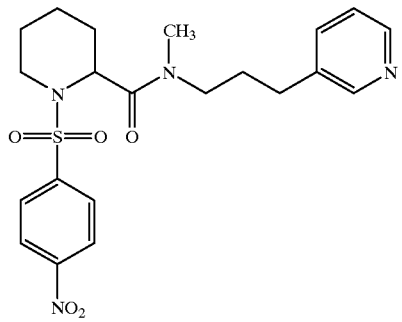

To a solution of the compound from step D (250 mg, 0.96 mmol) in methylene chloride (15 ml) was added triethylamine (2.0 ml, 101.19, 19.8 mmol) followed by the addition of 4-nitrobenzenesulfonylchloride (300 mg, 1.42 mmol). The mixture was allowed to stir at ambient temperature for 24 hours. The solution was diluted with 200 ml ethyl acetate and a saturated solution of sodium bicarbonate (50 ml). The separated organics were dried over anhydrous MgSO₄ and concentrated under reduced pressure. The crude product was purified via medium pressure liquid chromatography using a gradient solvent system of methylene chloride followed by 1:99 methanol/methylene chloride solution to give 165 mg (37% yield) of the title compound as a yellowish oil. TLC: Rf=0.52 (5:95 methanol/methylene chloride), [¹H]-NMR (CDCl₃) consistent with structure.

F. N-(4-nitrobenzenesulfonamido)-(S)-piperidine-2-carboxylic acid-((N-methyl)-3-(pyridin-3-yl)propyl) amide (compound 3).

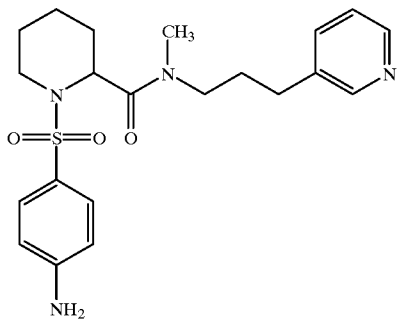

A solution of the compound from step E (165 mg, 0.35 mmol) in ethyl acetate (20 ml) was treated under ambient temperature with 150 mg of 10% palladium on carbon and hydrogenated for 24 hours under a slight positive pressure of hydrogen. The mixture was filtered and concentrated in vacuo and the crude product purified via medium pressure liquid chromatography using methylene chloride followed by 2:98 methanol/methylene chloride followed by 0.5:5:95 NH$_4$OH/methanol/methylene chloride solution as the solvent system to give 60 mg (41% yield) of the title compound as a yellowish oil. TLC: Rf=0.20 (5:95 methanol/methylene chloride), HPLC: Rt=7.25 min, [$^1$H]-NMR (CDCl$_3$) consistent with structure.

EXAMPLE 4

(S)-(N-Methyl)-2-(Methyl-(4-Amino-Benzenesulfanilamido))-3-Phenyl-N-(4-(Pyridin-3-Yl)-1-(3-(Pyridin-3-yl)Propyl) Butyl) provionamide The synthesis of (S)-(N-methyl)-2-(methyl-(4-amino-benzenesulfanilamido))-3-phenyl-N-(4-(pyridin-3-yl)-1-(3-(pyridin-3-yl)Propyl) butyl) propionamide is set forth below.

A. (S)-(N-methyl)-2-(methyl-2-tertbutyloxycarbonyl) amino)-3-phenyl-N-(4-(pyridin-3-yl)-1-(3-(pyridin-3-yl) propyl)butyl) propionamide.

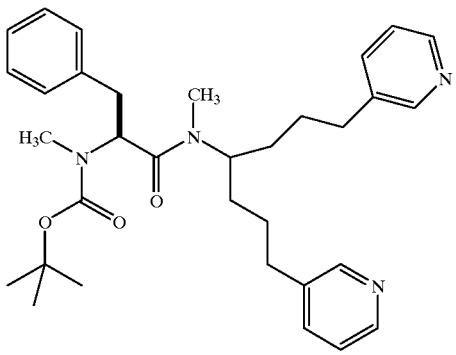

To a solution of Boc-(N-Methyl)phenylalanine (1.42 g, 5.1 mmol) in methylene chloride (10 ml) was added EDC (0.98 g, 191.71, 5.1 mmol) followed by the addition of N-methyl-1,7 bis(3-pyridyl)-4-heptylamine (1.2 g, 18.4 mmol). The mixture was allowed to stir at ambient temperature for 24 hours. The solution was diluted with 100 ml ethyl acetate and a saturated solution of sodium bicarbonate (50 ml). The separated organics were dried over anhydrous MgSO$_4$ and concentrated under reduced pressure. The crude product was purified via medium pressure liquid chromatography using 2:98 methanol/methylene chloride solution to give 970 mg (42% yield) of the title compound as a colorless oil. TLC: Rf=0.51 (5:95 methanol/methylene chloride), [$^1$H]-NMR (CDCl$_3$) consistent with structure.

B. (2S)-N-Methyl-2-methylamino-3-phenyl-N-[4-pyridin-3-yl-1-(3-pyridin-3-yl propyl)-butyl]-propionamide.

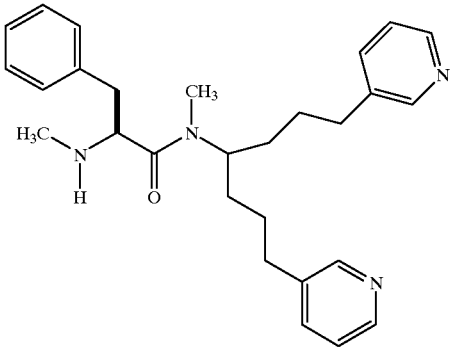

To the compound of step A (5.0 g, 9.2 mmol) in methylene chloride (20 ml) was added trifluoroacetic acid (20 ml, 260 mmol). The mixture was allowed to stir 3 hours at ambient temperature. The solution was concentrated under reduced pressure to dryness. The residue was taken up in ethyl acetate (200 ml) and a saturated solution of sodium bicarbonate (100 ml). The separated organics were dried over anhydrous MgSO$_4$ and concentrated under reduced pressure. The crude product was purified via medium pressure liquid chromatography using a gradient solvent system of 1:99 methanol/methylene chloride followed by 5:95 methanol/methylene chloride followed by 1:10:90 NH$_4$OH/methanol/methylene chloride) to give 3.12 g (76% yield) of the title compound as a colorless oil. TLC: Rf=0.38 (1:10:90 NH$_4$OH/methanol/methylene chloride). HPLC: Rt=9.52 min, [$^1$H]-NMR (CDCl$_3$) consistent with structure.

C. (S)-(N-methyl)-2-(methyl-(4-nitrobenzene-sulfanilamido))-3-phenyl-N-(4-(pyridin-3-yl)-1-(3-(pyridin-3-yl)propyl)Butyl) propionamide.

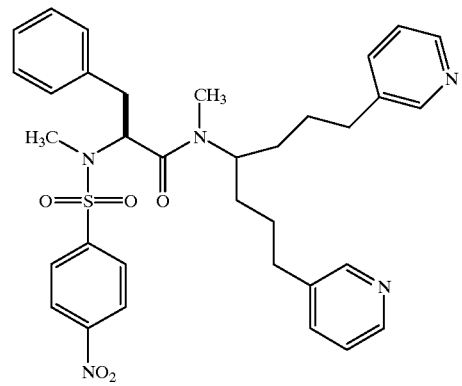

To a solution of the compound of step B (1.5 g, 3.4 mmol) in methylene chloride (20 ml) was added triethylamine (5.0 ml, 101.19, 35.8 mmol) followed by the addition of 4-nitrobenzenesulfonylchloride (1.0 g, 4.7 mmol). The mixture was allowed to stir at ambient temperature for 24 hours. The solution was diluted with 150 ml ethyl acetate and washed with water (50 ml). The separated organics were dried over anhydrous MgSO$_4$ and concentrated under reduced pressure. The crude product was purified via medium pressure liquid chromatography using a gradient solvent system of methylene chloride followed by 1:99 methanol/methylene chloride solution to give 1.75 g (83% yield) of the title compound as a yellowish oil. TLC: Rf=0.67 (5:95 methanol/methylene chloride), [$^1$H]-NMR (CDCl$_3$) consistent with structure.

D. (S)-(N-methyl)-2-(methyl-(4-aminobenzene-sulfanilamido))-3-phenyl-N-(4-(pyridin-3-yl)-1-(3-(pyridin-3-yl)propyl)butyl) propionamide (compound 4).

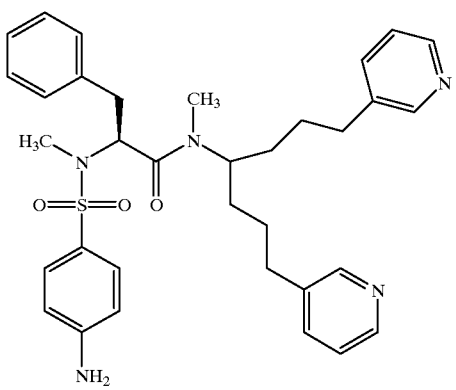

A solution of the compound of step C (1.75 g, 2.78 mmol) in ethyl acetate (50 ml) was treated under ambient temperature with 1.0 g of 10% palladium on carbon and hydrogenated for 24 hours under a slight positive pressure of hydrogen. The mixture was filtered and concentrated in vacuo and the crude product purified via medium pressure liquid chromatography using methylene chloride followed by 1:99 methanol/methylene chloride followed by 3:97 methanol/methylene chloride solution as the solvent system to give 0.79 mg (47% yield) of the title compound as a yellowish oil. TLC: Rf=0.36 (1:10:90 NH$_4$OH/methanol/methylene chloride). HPLC: Rt=7.97 min, [$^1$H]-NMR (CDCl$_3$) consistent with structure.

The synthesis of other compounds of this invention, including those listed in Table 1 above, may be achieved by modifying the synthesis schemes set forth in Examples 1–4 using appropriate reagents that are well known in the art.

EXAMPLE 5

(S)-Piperidine-2-Carboxylic Acid, (4-Pyridylmethyl) Amide, Citrate Salt

The synthesis of (S)-piperidine-2-carboxylic acid-1-(tert-butyl ester)-2-(4-pyridylmethyl) amide, citrate salt (compound 1) is set forth below.

A. (S)-piperidine-1,2-dicarboxylic acid-1-(tert-butyl ester)-2-(4-pyridylmethyl) amide

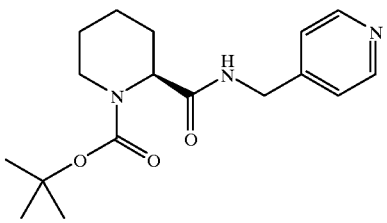

Following the method described in Example 1, part A, (S)-piperidine-1,2-dicarboxylic acid-1-(tert-butyl ester) (2.0 g, 8.72 mmol) and 4-(aminomethyl) pyridine (3.18 g, 29.41 mmol) was converted to 0.75 g (27% yield) of product. [$^1$H]-NMR (CDCl$_3$) consistent with structure.

B. (S)-Piperidine-2-Carboxylic acid, (4-Pyridylmethyl) Amide

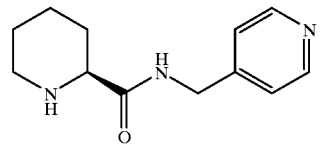

Following the method of Example 1, part B, (S)piperidine-1-carboxylic acid-1-(tert-butyl ester)-2-(4-pyridylmethyl) amide (0.75 g, 2.35 mmol) gave 0.49 g (95% yield) of the title compound. [$^1$H]-NMR (CDCl$_3$) consistent with structure.

C. (S)-Piperidine-2-Carboxylic acid, (4-Pyridylmethyl) Amide, Citrate Salt

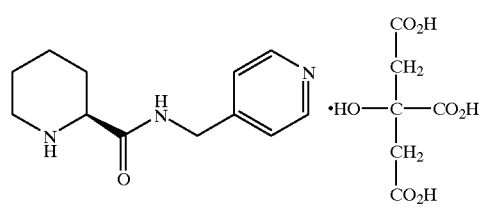

A solution of the amine (107 mg, 0.48 mmol) from part B and citric acid (94 mg, 0.48 mmol) in absolute ethanol was warmed to 60° C. until dissolved. The solution was concentrated in vacuo and the residue was dissolved in absolute ethanol and concentrated in vacuo to give a foam. [$^1$H]-NMR (CDCl$_3$) consistent with structure.

EXAMPLE 6

(S)-Piperidine-2-Carboxylic Acid, (4-Pyridylmethyl) Amide, Citrate Salt

The synthesis of (S)-piperidine-1,2-dicarboxylic acid-1-(tert-butyl ester)-2-(3-pyridylmethyl) amide, citrate salt is set forth below.

35

A. (S)-piperidine-1,2-dicarboxylic acid-1-(tert-butyl ester)-2-(3-pyridylmethyl) amide

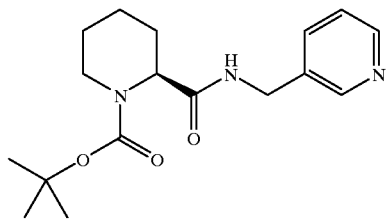

Following the method described in Example 1, part A, (S)-piperidine-1,2-dicarboxylic acid-1-(tert-butyl ester) (2.0 g, 8.72 mmol) and 3-(aminomethyl) pyridine (3.18 g, 29.41 mmol) was converted to 1.0 g (36% yield) of product. [$^1$H]-NMR (CDCl$_3$) consistent with structure.

B. (S)-Piperidine-2-Carboxylic acid, (3-Pyridylmethyl) Amide

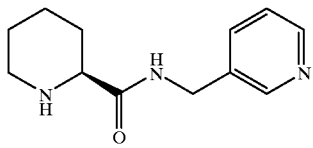

Following the method of Example 1, part B, (S)piperidine-1,2-dicarboxylic acid-1-(tert-butyl ester)-2-(3-pyridylmethyl) amide (1.0 g, 3.13 mmol) gave 0.56 g (82% yield) of the title compound. [$^1$H]-NMR (CDCl$_3$) consistent with structure.

C. (S)-Piperidine-2-Carboxylic acid, (2-Pyridylmethyl) Amide, Citrate Salt

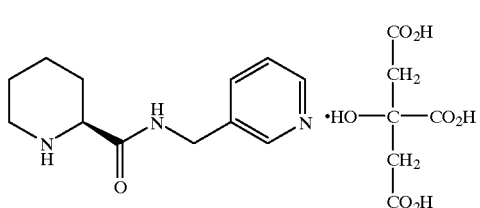

A solution of the amine (111 mg, 0.51 mmol) in part B and citric acid (97 mg, 0.51 mmol) was warmed to 60° C. until dissolved. The solution was concentrated in vacuo and the residue was dissolved in absolute ethanol and concentrated in vacuo to give a foam. [$^1$H]-NMR (CDCl$_3$) consistent with structure.

36

EXAMPLE 7

(S)-Piperidine-2-Carboxylic Acid-2-((N Methyl)-2-Pyridylethyl) Amide, Citrate Salt

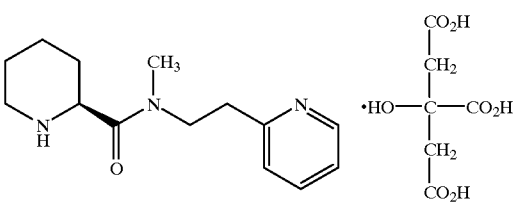

Following the method described in Example 5, part C, (S)-piperidine-2-carboxylic acid-2-((N methyl)-2-pyridylethyl) amide (product in example 1, part B) was converted to a citrate salt. [$^1$H]-NMR (CDCl$_3$) consistent with structure.

EXAMPLE 8

(S)-Piperidine-2-Carboxylic acid-((N-Methyl)-3-(Pyridin-3-yl)Propyl) Amide, Citrate Salt

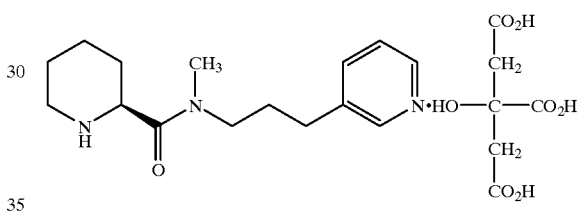

(S)-piperidine-2-carboxylic acid-((N-methyl)-3-(pyridin-3-yl)propyl) amide (product from Example 3, part D) was converted to a citrate salt. [$^1$H]-NMR (CDCl$_3$) consistent with structure.

EXAMPLE 9

(S)-Piperidine-2-Carboxylic Acid, (1,7-di-pyridin-3-yl)heptan-4-yl) ester, Fumarate Salt A. (S)-Piperidine-1,2-Dicarboxylic Acid-1-(Tert-Butyl ester)-2-(1,7-di-pyridin-3-yl)heptan-4-yl) ester

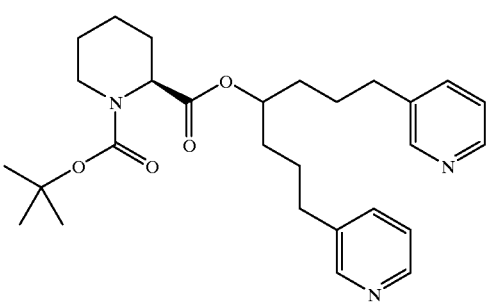

A solution of (1,7-di-pyridin-3-yl)heptan-4-ol (6.6 g, 24.41 mmol) in THF (30 ml) was added to (S)piperidine-1,2 dicarboxylic acid-1-(tert-butyl ester) (5.0 g, 21.81 mmol) and EDC (4.7 g, 24.52 mmol) and allowed to stir for 18 h at room temperature. The reaction was diluted with ethyl acetate (200 ml) and washed with water. The organic layer was dried over MgSO$_4$, concentrated in vacuo and purified by medium pressure liquid chromatography using 1:100 methanol/methylene chloride as the solvent system to give 2.0 g (20% yield) of the title compound. [$^1$H]-NMR (CDCl$_3$) consistent with structure.

B. (S)-Piperidine-2-Carboxylic Acid, (1,7-dipyridin-3-yl)heptan-4-yl) ester

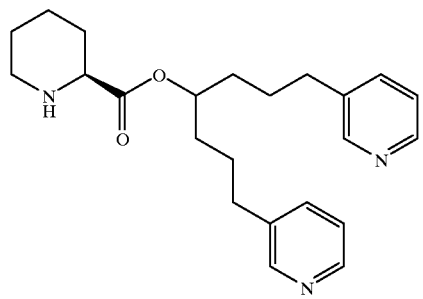

Following the method of Example 1, part B, the compound from Example 10, part A, (1.0 g, 4.30 mmol) gave 1.45 g (88% yield) of the title compound. [$^1$H]-NMR (CDC$_3$) consistent with structure.

C. (S)-Piperidine-2-Carboxylic Acid, (1,7-dipyridin-3-yl)heptan-4-yl) ester, Bis-fumarate Salt

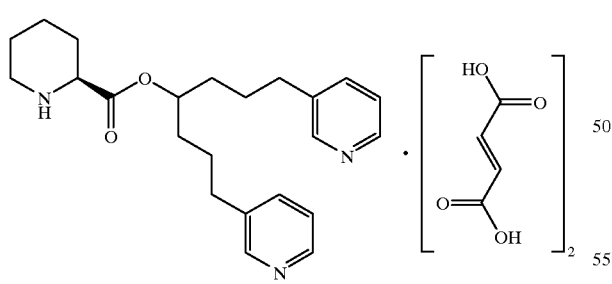

Following the procedure in Example 6, part C, the amine in example 10, part C may be converted to the title compound using 1 equivalent of the amine and two equivalents of fumaric acid. [$^1$H]-NMR (CDCl$_3$) consistent with structure.

EXAMPLE 10

(S)-1-Methyl-Piperidine-2-Carboxylic Acid, (1,7-dipyridin-3-yl)heptan-4-yl) ester

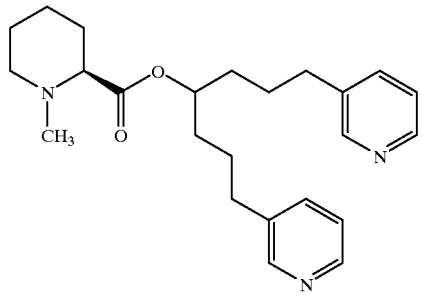

A mixture of the amine (300 mg, 0.79 mmol) from Example 10, part B and paraformaldehyde (500 mg) in methanol (15 ml) was added to Na(CN)BH$_3$ (500 mg). The mixture was stirred for 65 h at room temperature. The reaction was concentrated in vacuo and taken up in 2N aqueous NaOH and extracted with ethyl acetate (150 ml). The organic layer was dried over MgSO$_4$, concentrated in vacuo and purified by medium pressure liquid chromatography using a gradient solvent system of 2:98 methanol/methylene chloride followed by 0.5:5:95 NH$_4$OH/methanol/methylene chloride to give 230 mg (74% yield) of the title compound as a clear oil. [$^1$H]-NMR (CDCl$_3$) consistent with structure.

EXAMPLE 11

(S)-1-(2-Methylpropyl)-Piperidine-2-Carboxylic Acid, (1,7-di-pyridin-3-yl)heptan-4-yl) ester

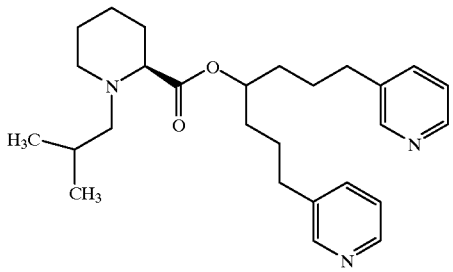

Following the method described in Example 11, mixture of the amine (300 mg, 0.79 mmol) from Example 10, part B and 2-methylpropionaldehyde (1.6 g, 22.0 mmol) in methanol (15 ml) was added to Na(CN)BH$_3$ (500 mg). The mixture was stirred for 65 h at room temperature. The reaction was concentrated in vacuo and taken up in 2N aqueous NaOH (20 ml) and extracted with ethyl acetate (150 ml). The organic layer was dried over MgSO$_4$, concentrated in vacuo and purified by medium pressure liquid chromatography using a gradient solvent system of 2:98 methanol/ methylene chloride followed by 0.5:5:95 NH$_4$OH/methanol/ methylene chloride to give 170 mg (49% yield) of the title compound as a clear oil. [$^1$H]-NMR (CDCl$_3$) consistent with structure.

EXAMPLE 12

(S)-1-(Pyridin-4-ylmethyl)-Piperidine-2-Carboxylic Acid (1,7-di-pyridin-3-yl)heptan-4-yl) ester

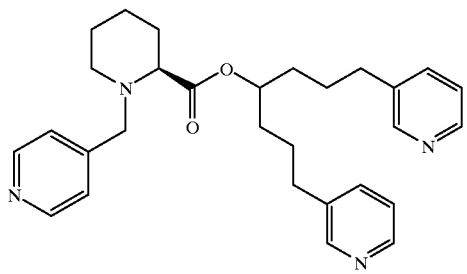

Following the method described in Example 11, mixture of the amine (300 mg, 0.79 mmol) from Example 10, part B and 4-pyridinecarboxaldehyde (0.5 g, 4.67 mmol) in methanol (15 ml) was added to Na(CN)BH$_3$ (500 mg). The mixture was stirred for 65 h at room temperature. The reaction was concentrated in vacuo and taken up in 2N aqueous NaOH (20 ml) and extracted with ethyl acetate (150 ml). The organic layer was dried over MgSO$_4$, concentrated in vacuo and purified by medium pressure liquid chromatography using a gradient solvent system of 2:98 methanol/ methylene chloride followed by 0.5:5:95 NH$_4$OH/methanol/ methylene chloride to give 70 mg (19% yield) of the title compound as a clear oil. [$^1$H]-NMR (CDCl$_3$) consistent with structure.

EXAMPLE 13

(S)-(N-Methyl)-2-(Methylamino)-3-Phenyl-N-(2-(Pyridin-2-yl)ethyl) Propionamide, Citrate Salt

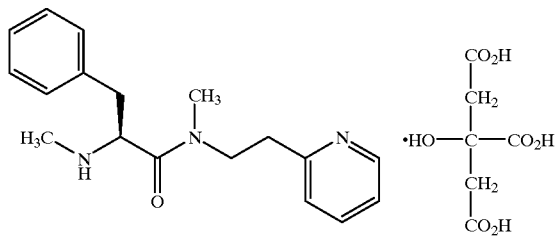

Following the method described in Example 6, part C, (N-methyl)-2-(methylamino)-3-phenyl-N-(2-(pyridin-2-yl) ethyl) propionamide (product in Example 2, part B) was converted to a citrate salt. [$^1$H]-NMR (CDCl$_3$) consistent with structure.

EXAMPLE 14

(2S)-N-Methyl-2-Methylamino-3-Phenyl-N-[4-Pyridin-3-yl-1-(3-Pyridin-3-yl propyl)-butyl]-propionamide, Citrate Salt.

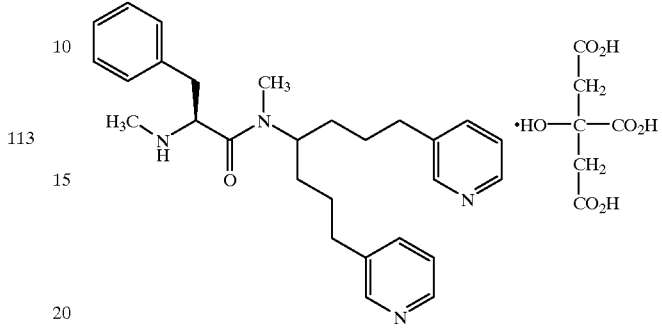

Following the method described in Example 6, part C, (2S)-N-Methyl-2-methylamino-3-phenyl-N-[4-pyridin-3-yl-1-(3-pyridin 3-yl-propyl)-butyl]propionamide (product in Example 4, part B) was converted to a citrate salt. [$^1$H]-NMR (CDC$_3$) consistent with structure.

EXAMPLE 15

Rotamase Inhibition Assay

Inhibition of FKBP enzyme activity was determined in the PPIase assay described in S. T. Park et al., *J. Biol. Chem.*, 267, pp. 3316–24 (1992), the disclosure of which is herein incorporated by reference. This is a chymotrypsin-coupled assay in which FKBP catalyzes the cis to trans isomerization of the Leu-Pro bond in the peptide substrate Suc-Ala-Leu-Pro-Phe-pNA. The trans form, but not the cis form, is cleavable by chymotrypsin. The release Phe-pNA was monitored by absorbance at 400 nm. Chymotrypsyn cleavage is very rapid and therefore cis-to-trans isomerization is rate-limiting.

Each reaction mix consisted of 0.1 M Tris buffer, pH 7.8, 15 nM FKBP, 30 $\mu$M substrate and 0.5 nM to 10 $\mu$M of compound to be tested diluted in Me$_2$SO. The mixture was incubated at 15° C. for 5 minutes and then reaction was initiated by addition of chymotrypsin (100 $\mu$g/ml final concentration) and followed spectrophotometrically for 5 minutes. Total reaction volume was 1 ml. None of the compounds of this invention demonstrated a Ki of less than 10 $\mu$M, as demonstrated in the table below.

TABLE 4

| Rotamase Inhibition. | |
| --- | --- |
| Compound # | Rotamase Inhibition (Ki) (nM) |
| 2 | >50,000 |
| 3 | >50,000 |
| 4 | >25,000 |
| 8 | >50,000 |
| 18 | >50,000 |
| 101 | >50,000 |
| 103 | >50,000 |
| 104 | >50,000 |
| 106 | >50,000 |

TABLE 4-continued

Rotamase Inhibition.

| Compound # | Rotamase Inhibition (Ki) (nM) |
| --- | --- |
| 107 | >25,000 |
| 108 | >25,000 |
| 110 | >25,000 |
| 111 | >50,000 |
| 112 | >50,000 |
| 113 | >50,000 |

EXAMPLE 16

MDR Sensitization Assay

To demonstrate that the compounds according to this invention do not possess MDR reversal activity, cell lines which are known to be resistant to a particular drug were used.

We carried out multidrug resistance reversal (MDR) assays using L1210vMDRC.06 or HL60/Vinc cell lines. L1210vMDRC.06 are L1210 mouse leukemia cells transduced with the pHaMDR1/A retrovirus carrying a MDR1 cDNA, as described by Pastan et al., *Proc. Natl. Acad. Sci. USA*, 85, pp. 4486–4490 (1988). The L1210vMDRC.06 multidrug resistant line is a cell line that has been drug-selected by culturing transfected cells in 0.06 $\mu$g/ml colchicine. The HL60/Vinc human promyleocytic leukemia cell line is a multidrug resistant cell line derived from HL60 drugsensitive parental cells by selection in increasing concentrations of vincristine.

Using L1210vMDRC.06, multidrug resistance reversal assays were conducted by plating $1 \times 10^4$ cells/well in 96 well microtiter plates and exposing them to a concentration range of doxorubicin (50 nM–10 $\mu$M) in the presence or absence of compounds of this invention (0.1, 0.25, 0.5, 1.0, or 2.5 $\mu$M) as described in U. Germann et al., *Anti-Cancer Drugs*, 8, pp. 125–140 (1997). After culture for 3 days, the viability of cells was quantitated using XTT dye to assess mitochondrial function [Roehm et al., *J. Immunol. Methods*, 142, pp. 257–265, (1991)]. All determinations were made in replicates of at least 4. Results were determined by comparison of the IC50 for doxorubicin alone to the IC50 for doxorubicin+compound. An MDR ratio was calculated (IC50 Dox/IC50 Dox+Inhibitor) and the integer value used for comparison of compound potencies.

Assays using HL60/Vinc cells were performed by plating cells in 96 well microtiter plates at a concentration of 4x104 cells/well. The cells were then exposed to various concentrations of doxorubicin (9 nM to 6.7 $\mu$M) in the presence or absence of various compounds of this invention at various concentrations (0.5, 1.0, 2.5, 5.0 or 10 $\mu$M) as described in U. Germann et al., *Anti-Cancer Druqs*, 8, pp. 141–155 (1997). After culturing the cells for 3 days, their viability was quantitated using the XTT dye method to assess mitochondrial function (Roehm et al., supra). Results were expressed as a ratio of the IC50 for doxorubicin alone to the IC50 for doxorubicin plus compound. In all assays the intrinsic antiproliferative or cytotoxicity activity of the MDR inhibitors was also determined for HL60/Vinc cells.

The results of these assays on several compounds of this invention are depicted in the table below.

TABLE 5

MDR Reversal Assay.

| Compound # | MDR Ratio* | Cell line |
| --- | --- | --- |
| 1 | 0.6 | HL60/Vinc |
| 2 | 0.7 | HL60/Vinc |
| 3 | 0.6 | HL60/Vinc |
| 4 | 6.2 | HL60/Vinc |
| 5 | 30.4 | HL60/Vinc |
| 6 | 17.7 | HL60/Vinc |
| 7 | 21.9 | HL60/Vinc |
| 8 | 28.5 | HL60/Vinc |
| 9 | 24.3 | HL60/Vinc |
| 10 | 9.1 | HL60/Vinc |
| 11 | 1.7 | HL60/Vinc |
| 12 | 22.6 | HL60/Vinc |
| 13 | 19.3 | HL60/Vinc |
| 14 | 19.9 | HL60/Vinc |
| 15 | 2.4 | HL60/Vinc |
| 16 | 19.9 | HL60/Vinc |
| 17 | 14.6 | HL60/Vinc |
| 18 | 10.8 | HL60/Vinc |
| 102 | 1.2 | HL60/Vinc |
| 103 | 0.7 | HL60/Vinc |
| 104 | 0.6 | HL60/Vinc |
| 105 | 10 | L1210vMDRC.06 |
| 106 | 1.2 | HL60/Vinc |
| 107 | 0.9 | HL60/Vinc |
| 108 | 0.4 | HL60/Vinc |
| 110 | 1.1 | HL60/Vinc |
| 111 | 1.2 | HL60/Vinc |
| 112 | 2.4 | HL60/Vinc |
| 113 | 2.3 | HL60/Vinc |

*MDR ratios tested at compound concentrations of 2.5 $\mu$M, except for compounds 5, 6 and 7, which were tested at 10 $\mu$M.

As can be seen from these results, there does not seem to be a strong correlation between structure and MDR ratio. Factors which could be responsible for this are the ability of the compound to get into the cell, the toxicity of the compound and the metabolism of the compound inside the cell. As such, compounds with an MDR ratio higher than 7 would not be included as compounds which lacks MDR reversal activity according to the parameters of this invention.

EXAMPLE 17

Neurite Outgrowth puantitation In PC12 Cell System

In order to directly determine the neurotrophic activity of compounds described in this invention, the neurite outgrowth assay was carried out with pheochromocytoma PC12 cells as described by Lyons et al. (1994).

PC12 cells were maintained at 37° C. and 5% $CO_2$ in Dulbecco's modified Eagle's medium (DMEM) supplemented with 10% heat-inactivated horse serum, 5% heat-inactivated fetal bovine serum (FBS), and 1% glutamate.

The cells were then plated at 105 per well in 96 well plates coated with 5 m/cm2 rat tail collagen and allowed to attach overnight. The medium was then replaced with DMEM, 2% heat-inactivated horse serum, 1% glutamate, 1–5 ng/ml of NGF (Sigma) and varying concentrations of the compounds of this invention (0.01 nM–10000 nM). The background control culture was administered with 105 ng/ml of NGF alone without compound. Positive control cultures were administered with high concentration of NGF (50 ng/ml). The cells were then incubated at 37° C. at 5% $CO_2$ for 72 hours, fixed with 3% formaldehyde and nerve outgrowth was determined visually on a scale of 0 to 4.

The results are shown in the table below.

TABLE 6

Neurite Outgrowth Activity of Compounds of this Invention.

| Compound | 0.01 nM | 0.1 nM | 1 nM | 10 nM | 100 nM | 1000 nM | 10000 nM |
|---|---|---|---|---|---|---|---|
| 1 | ND | ND | ND | 3*** | 1*** | 3*** | ND |
| 2 | ND | ND | ND | 3*** | 3*** | 4*** | ND |
| 3 | ND | ND | ND | 2*** | 4*** | 4*** | ND |
| 4 | ND | ND | ND | 3* | 3* | 4* | ND |
| 5 | ND | ND | ND | 2* | 3* | 3* | ND |
| 6 | ND | ND | ND | 4* | 2* | 3* | ND |
| 7 | ND | ND | ND | 2* | 3* | 3* | ND |
| 8 | ND | ND | ND | 4* | 2* | 3* | ND |
| 9 | ND | ND | ND | 4* | 2* | 3* | ND |
| 10 | ND | ND | ND | 3* | 4* | 2* | ND |
| 11 | ND | ND | ND | 1* | 3* | 3* | ND |
| 12 | ND | ND | ND | 3* | 3* | 4* | ND |
| 13 | ND | ND | ND | 3* | 3* | 4* | ND |
| 14 | ND | ND | ND | 3* | 2* | 4* | ND |
| 15 | ND | ND | ND | 3* | 3* | 3* | ND |
| 16 | ND | ND | ND | 3* | 4* | 3* | ND |
| 17 | ND | ND | ND | 3* | 3* | 4* | ND |
| 18 | ND | ND | ND | 3* | 4* | 4* | ND |
| 101 | ND | ND | ND | ND | ND | ND | ND |
| 102 | 3* | 3* | 4* | 4** | 2** | 3** | 4* |
| 103 | ND | ND | ND | 0 | 0 | 0 | ND |
| 104 | 3* | 3* | 2* | 2* | 4* | 3* | 4* |
| 105 | ND | ND | ND | 4 | 4 | 0 | ND |
| 106 | ND | ND | ND | ND | 1* | 2* | ND |
| 107 | ND | ND | ND | ND | 3* | 0* | ND |
| 108 | ND | ND | ND | 0 | 3 | 0 | ND |
| 109 | 3* | 4* | 4* | 3* | 2* | 4* | 3* |
| 110 | ND | ND | ND | ND | 3* | 0* | ND |
| 111 | 4* | 4* | 3* | 2** | 4** | 4** | 4* |
| 112 | ND | ND | ND | 3* | 4* | 3* | ND |
| 113 | ND | ND | ND | 3* | 4* | 4* | ND |

*Asaay done in triplicate for each concentration tested. Indicated result is average of the three samples.
**Assay repeated twice, each time in triplicate. Indicated result is average of the six samples.
***Assay done in quadruplicate for each concentration tested. Indicated result is average of the three samples.

The compounds of this invention as exemplified by compounds 1–18, 101 and 103–113 caused a significant increase in neurite outgrowth over background control cultures. Lack of nerve growth stimulatory activity (as indicated by the "0") at high compound concentrations of certain compounds is attributed to the toxic effects of those compounds on the cells at higher concentrations. Negative results for compound 103 were the result of only a single experiment with one sample assayed at each of 3 concentrations. We believe this compound will display some nerve growth stimulatory activity in the PC12 assay when this experiment is repeated.

Other compounds of this invention will also demonstrate significant nerve growth stimulatory activity.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:
1. A compound of the formula:

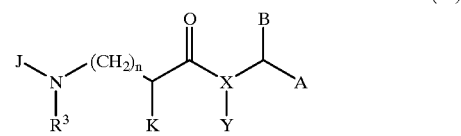

(III)

and pharmaceutically acceptable derivatives thereof, wherein:
A and B are independently selected from Ar-substituted-$(C_1–C_6)$-straight or branched alkyl, or Ar-substituted-$(C_2–C_6)$-straight or branched alkenyl or alkynyl;
Ar is selected from 2-pyridyl, 3-pyridyl, or 4-pyridyl; and wherein
each Ar is optionally substituted with one to three substituents independently selected from halogen, hydroxyl, nitro, —$SO_3H$, trifluoromethyl, trifluoromethoxy, $(C_1–C_6)$-straight or branched alkyl, $(C_2–C_6)$-straight or branched alkenyl, O-(($C_1–C_6)$-straight or branched alkyl), O-(($C_2–C_6)$-straight or branched alkenyl), O-benzyl, O-phenyl, 1,2-methylenedioxy, —$N(R^1)$ $(R^2)$, carboxyl, N-($C_1–C_5$-straight or branched alkyl or $C_2–C_5$-straight or branched alkenyl) carboxamide, N,N-di-($C_2–C_5$-straight or branched alkyl or $C_2–C_5$-straight or branched alkenyl) carboxamide, N-($C_1–C_5$straight or branched alkyl or $C_2$–$C_5$-straight or branched alkenyl) sulfonamide, N,N-di-($C_1$–$C_5$-straight or branched alkyl or $C_2$–$C_5$-straight or branched alkenyl) sulfonamide, morpholinyl, piperidinyl, O—Z, $CH_2$—$(CH_2)_q$—Z, O—$(CH_2)_q$—Z, $(CH_2)_q$—Z—O—Z, or CH=CH—Z;

wherein $R^1$ and $R^2$ are independently selected from ($C_1$–$C_6$)-straight or branched alkyl, ($C_2$–$C_6$)-straight or branched alkenyl or alkynyl, hydrogen or benzyl; or wherein $R_1$ and $R_2$ are taken together with the nitrogen atom to which they are bound to form a 5–7 membered heterocyclic ring;

Z is selected from 2-pyridyl, 3-pyridyl, or 4-pyridyl; and q is 0, 1 or 2;

X is N, O or C(R);

wherein R is selected from hydrogen, ($C_1$–$C_6$)-straight or branched alkyl, or ($C_2$–$C_6$)-straight or branched alkenyl or alkynyl;

wherein when X is N or C(R), Y is selected from hydrogen, Ar, ($C_1$–$C_6$)-straight or branched alkyl, ($C_2$–$C_6$)-straight or branched alkenyl or alkynyl, ($C_5$–$C_7$)-cycloalkyl-substituted-($C_1$–$C_6$)-straight or branched alkyl, ($C_5$–$C_7$)cycloalkyl-substituted-($C_2$–$C_6$)-straight or branched alkenyl or alkynyl, ($C_5$–$C_7$)-cycloalkenyl-substituted-($C_1$–$C_6$)-straight or branched alkyl, ($C_5$–$C_7$)-cycloalkenyl-substituted-($C_2$–$C_6$)-straight or branched alkenyl or alkynyl, Ar-substituted-($C_1$–$C_6$)-straight or branched alkyl, Ar-substituted-($C_2$–$C_6$)-straight or branched alkenyl or alkynyl, phenyl substituted($C_1$–$C_6$)-straight or branched alkyl, or phenyl substituted-($C_2$–$C_6$)-straight or branched alkenyl or alkynyl;

when X is O, Y is a lone pair of electrons;

K is selected from ($C_1$–$C_6$)-straight or branched alkyl, Ar-substituted-($C_1$–$C_6$)-straight or branched alkyl, ($C_2$–$C_6$)-straight or branched alkenyl or alkynyl, Ar-substituted-($C_2$–$C_6$)-straight or branched alkenyl or alkynyl, phenyl substituted-($C_1$–$C_6$)-straight or branched alkyl, phenyl substituted-($C_2$–$C_6$)-straight or branched alkenyl or alkynyl, or cyclohexylmethyl; wherein any one of the $CH_2$ groups of said alkyl, alkenyl or alkynyl chains in K is optionally replaced by O, S, S(O), $S(O)_2$ or N(R);

n is 0, 1 or 2;

J is selected from hydrogen, ($C_1$–$C_6$)-straight or branched alkyl, ($C_2$–$C_6$)-straight or branched alkenyl or alkynyl, Ar-substituted-($C_1$–$C_6$)-straight or branched alkyl, Ar-substituted-($C_2$–$C_6$)-straight or branched alkenyl or alkynyl, phenyl substituted-($C_1$–$C_6$)-straight or branched alkyl, phenyl substituted-($C_2$–$C_6$)-straight or branched alkenyl or alkynyl, or cyclohexylmethyl;

$R^3$ is selected from ($C_1$–$C_6$)-straight or branched alkyl, Ar-substituted-($C_1$–$C_6$)-straight or branched alkyl, ($C_2$–$C_6$)-straight or branched alkenyl or alkynyl, Ar-substituted-($C_2$–$C_6$)-straight or branched alkenyl or alkynyl, phenyl substituted-($C_1$–$C_6$)-straight or branched alkyl, or phenyl substituted-($C_2$–$C_6$)-straight or branched alkenyl or alkynyl;

wherein any one of the $CH_2$ groups of said alkyl, alkenyl or alkynyl chains in $R^3$ is optionally replaced by O, S, S(O), or N(R); and wherein any one of the $CH_2$ groups of said alkyl, alkenyl or alkynyl in $R^3$, except the $CH_2$ group bound to nitrogen, is optionally replaced with C(O) or $S(O)_2$.

2. The compound according to claim 1, wherein at least one of A or B is an Ar-substituted ($C_1$–$C_6$)-alkyl chain.

3. The compound according to claim 2, wherein at least one of A or B is a ($C_1$–$C_6$)-alkyl chain terminally substituted with pyridinyl.

4. The compound according to claim 1, wherein X is N or O.

5. The compound according to claim 1, wherein K is benzyl.

6. The compound according to claim 1, wherein J is hydrogen or methyl.

7. The compound according to claim 1, wherein $R^3$ is selected from hydrogen, ($C_1$–$C_6$)-alkyl, ($C_1$–$C_6$)-alkyl terminally substituted with pyridyl, or 3,4,5-trimethyoxybenzoylmethyl.

8. The compound according to claim 1, wherein n is 0.

9. The compound according to claim 1, wherein said compound is (2S)-N-Methyl-2-methylamino-3-phenyl-N-[4-pyridin-3-yl-1-(3-pyridin-3-yl-propyl)-butyl]-propionamide.

10. A composition comprising:
a) a neurotrophic amount of a compound according to claim 1; and
b) a pharmaceutically suitable carrier.

* * * * *